US012161440B2

(12) United States Patent
Sin Kwok Wong et al.

(10) Patent No.: US 12,161,440 B2
(45) Date of Patent: Dec. 10, 2024

(54) DERIVING CONNECTIVITY DATA FROM SELECTED BRAIN DATA

(71) Applicant: Omniscient Neurotechnology Pty Limited, Sydney (AU)

(72) Inventors: Bryan Sin Kwok Wong, Toronto (CA); Xinling Jiang, Willoughby (AU); Michael Edward Sughrue, Brighton le Sands (AU); Stephane Philippe Doyen, Mount Kuring Gai (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/686,204

(22) Filed: Mar. 3, 2022

(65) Prior Publication Data

US 2023/0277061 A1    Sep. 7, 2023

(51) Int. Cl.
*A61B 5/00*      (2006.01)
*A61B 5/055*     (2006.01)
(Continued)

(52) U.S. Cl.
CPC ............ *A61B 5/0042* (2013.01); *A61B 5/055* (2013.01); *A61B 5/7425* (2013.01); *A61B 5/748* (2013.01);
(Continued)

(58) Field of Classification Search
CPC ..... A61B 5/0042; A61B 5/055; A61B 5/7425; A61B 5/748; A61B 2576/026;
(Continued)

(56) References Cited

U.S. PATENT DOCUMENTS

2007/0127793 A1* 6/2007 Beckett ................. G06T 7/0012
                                                              382/128
2011/0301431 A1* 12/2011 Greicius ............ G01R 33/4806
                                                              600/300

(Continued)

FOREIGN PATENT DOCUMENTS

JP          2017051599 A  *  3/2017  ............. A61B 5/055

OTHER PUBLICATIONS

Fan, L., Li, H., Zhuo, J., Zhang, Y., Wang, J., Chen, L., . . . & Jiang, T. (2016). The human brainnetome atlas: a new brain atlas based on connectional architecture. Cerebral cortex, 26(8), 3508-3526. (Year: 2016).*
JP2017051599A—machine translation (Year: 2017).*
Rubinov, M., & Sporns, O. (2010). Complex network measures of brain connectivity: uses and interpretations. Neuroimage, 52(3), 1059-1069. (Year: 2010).*

(Continued)

*Primary Examiner* — Jason M Ip
*Assistant Examiner* — Renee C Langhals
(74) *Attorney, Agent, or Firm* — Fish & Richardson P.C.

(57) ABSTRACT

Disclosed are techniques for identifying and displaying spatial relationships between a seed parcel and other parcels in a patient's brain. A method can include obtaining connectivity data characterizing, for each pair of parcels including a first parcel and a second parcel from a group of parcels, a connectivity metric measuring a relationship between the first and second parcels in the patient's brain, obtaining brain atlas data, identifying a seed parcel from the group of parcels, determining one or more other parcels in the group of parcels having a connectivity metric with the seed parcel that satisfies a threshold connectivity metric condition to provide at least one seed-connected parcel, and for the seed-connected parcel, providing the brain atlas data and an indication of a degree of the connectivity metric between the seed parcel and seed-connected parcel for display as an overlay on a visualization of the brain atlas data.

18 Claims, 12 Drawing Sheets

(51) Int. Cl.
  *G01R 33/48* (2006.01)
  *G06F 3/0482* (2013.01)
  *G06F 3/04847* (2022.01)

(52) U.S. Cl.
  CPC ....... *G01R 33/4806* (2013.01); *G06F 3/0482* (2013.01); *G06F 3/04847* (2013.01); *A61B 2576/026* (2013.01); *G06F 2203/04803* (2013.01)

(58) Field of Classification Search
  CPC ............ G01R 33/4806; G01R 33/5608; G06F 3/0482; G06F 3/04847; G06F 2203/04803; G06T 7/0012; G06T 7/11; G06T 2207/10088; G06T 2207/20128; G06T 2207/30016; G16H 30/40; G16H 50/20
  See application file for complete search history.

(56) References Cited

U.S. PATENT DOCUMENTS

| | | | | |
|---|---|---|---|---|
| 2012/0271189 | A1* | 10/2012 | Nelson | A61N 1/36139 600/544 |
| 2015/0272493 | A1* | 10/2015 | Liu | A61B 5/055 600/410 |
| 2017/0071471 | A1* | 3/2017 | Yamagata | A61B 5/4029 |
| 2020/0352443 | A1* | 11/2020 | Fox | A61B 5/7425 |
| 2022/0180487 | A1* | 6/2022 | Sjöstrand | G06T 5/009 |
| 2022/0249168 | A1* | 8/2022 | Besier | A61B 6/468 |

OTHER PUBLICATIONS

Brinnetome Atlas, 2016, http://atlas.brainnetome.org/bnatlas.html (Year: 2016).*

* cited by examiner

DERIVING CONNECTIVITY DATA FROM SELECTED BRAIN DATA

BACKGROUND

This document generally relates to processing data related to the brain of a patient, e.g., functional magnetic resonance imaging (MRI) data and/or tractography data.

Brain functional connectivity data characterizes, for each of one or more pairs of locations within the brain of a patient, the degree to which brain activity in the pair of locations is correlated.

One can gather data related to the brain of the patient by obtaining and processing images of the brain of the patient, e.g., using magnetic resonance imaging (MM), diffusion tensor imaging (DTI), or functional MM imaging (fMRT). Diffusion tensor imaging uses magnetic resonance data to measure diffusion of water in a human brain. One can use the measured diffusion to generate tractography data, which can include images of neural tracts and corresponding white matter fibers of the subject brain.

Data related to the brain of a single patient can be highly complex and high-dimensional, and therefore difficult for a clinician to manually inspect and parse, e.g., to plan a surgery or diagnose the patient for a brain disease or mental disorder.

SUMMARY

This document generally relates to systems and techniques that can be used to select, derive, and view correlations, anomalies, or other connectivity metrics amongst parcels in a patient's brain. More specifically, the disclosed technology can provide graphical user interface (GUI) displays to a user at a user device for identifying a seed parcel, determining spatial relationships between the seed parcel and other parcels in the patient's brain, and providing those spatial relationships in the GUI displays at the user device. The user, such as a surgeon, clinician, or other medical professional, can interact with the information presented in the GUI displays to engage in improved, quick, and efficient analysis of functional MM data. Functional MM data is already 4-dimensional (4D) in nature, and additional analysis tends to add more dimensions of information, which can be hard to visualize, let alone understand, when the information is inherently spatially-related (e.g., relative to brain anatomy and connections). Accordingly, the disclosed technology provides digestible and interactive GUI displays of parcels in the patient's brain data for use by medical professionals to accurately and efficiently analyze the patient's brain and determine treatments, therapies, or diagnoses for that patient (e.g., high-precision targeted treatment of the brain such as transcranial magnetic stimulation (TMS)).

The user can inspect functional MRI data in two-dimensional (2D) and/or three-dimensional (3D) space in terms of parcels. The parcels, as described further below, can be groups of voxels that are logically grouped by some method (e.g., function, anatomical relevance, etc.). The user can also interact with the functional MRI data in 2D and/or 3D space. Possible interactions can include changing a seed parcel to a new parcel. The seed parcel can be a parcel relative to which visualized information is displayed. Similarly, the user can identify/select the seed parcel by selecting and viewing a column of a connectivity matrix, which can also be presented to the user with the patient brain data in 2D and/or 3D space. For example, a connectivity matrix, e.g., a correlation matrix of fMRI data, of the brain of a patient can be a matrix with more than a hundred, more than a thousand, or more than 10,000 matrix elements (e.g., having more than 10 or more than 100 rows and columns). Another interaction can include selecting and exporting one or more target parcels, which may or may not include the seed parcel. Another possible interaction can include removing a parcel from a current view of the brain data presented to the user in 2D and/or 3D space. Moreover, another interaction can include selecting or hovering over a parcel to identify the parcel's name and other relevant identifying information. Moreover, the disclosed technology can provide a legend for presentation with the brain data in 2D and/or 3D space, which can be used by the user to visualize different aspects of the brain data in various different ways. For example, the legend can include filters, such as sliders, that allow the user to refine what parcels and/or connectivity metrics amongst seed parcel and seed-connected parcels are displayed in 2D and/or 3D space.

As described herein, brain data can be any data characterizing the brain of a patient. For example, brain data can include one or both of i) direct measurement data of the brain of the patient, e.g., images of the brain collected using brain imaging techniques, or ii) data that has been derived or generated from initial measurement data of the brain of the patient, e.g., correlation matrices. Moreover, a parcel is a predefined region of the brain. For example, a parcel can be defined by boundaries on a 3D volume of the brain. A parcel can be defined such that the neurons in the parcel are functionally similar according to one or more criteria. For example, a set of parcels can be defined according to changes in cortical architecture, function, connectivity, and/or topography. A brain atlas is data that defines one or more parcels of a brain of a patient, e.g., by defining coordinates of the outline of the parcel or the volume of the parcel in a common three-dimensional coordinate system. Furthermore, data can be any data that defines a particular region of the brain for targeted treatment. For example, target data can identify one or more particular parcels of the brain of a patient, e.g., parcels as defined by a brain atlas. In some cases, target data can be provided to one or more medical devices for executing treatment of the patient, e.g., target data can be provided to an image guidance system for delivering treatment to the patient. Furthermore, a set of brain data can be considered anomalous if the values of the brain data are outside a normal range of values, e.g., as defined by a data set that includes brain data corresponding to multiple other patients, e.g., multiple other patients not known to have anomalous brain data.

One or more embodiments described herein can include a method including obtaining connectivity data characterizing, for each pair of parcels including a first parcel and a second parcel from a group of parcels, a connectivity metric measuring a relationship between the first parcel and the second parcel in a brain of a patient, obtaining brain atlas data, identifying a seed parcel from the group of parcels, determining one or more other parcels in the group of parcels having a connectivity metric with the seed parcel that satisfies a threshold connectivity metric condition to provide at least one seed-connected parcel, and for the seed-connected parcel, providing the brain atlas data and an indication of a degree of the connectivity metric between the seed parcel and the seed-connected parcel for display to a user as an overlay on a visualization of the brain atlas data.

In some implementations, the embodiments described herein can optionally include one or more of the following features. For example, the method can also include providing connectivity matrix data for display to a user, the connectivity matrix data being based on the connectivity data. The method can also include receiving a selection of a seed parcel. In some implementations, the method can include receiving a filter criteria for the connectivity metric. The selection can be a user selection of a column or a row of the connectivity matrix data. The selection can also be a user selection of a parcel from the group of parcels visualized as the overlay over the brain atlas data. The connectivity metric can be based on a correlation of BOLD signals variation over time. The connectivity metric can be a degree to which the correlation of BOLD signals is anomalous. The connectivity metric can also be based on a number of tracts connecting the first parcel and the second parcel. In some implementations, identifying the seed parcel can include identifying the seed parcel as a user-selected parcel that is overlaid on the visualization of the brain atlas data. Moreover, the method can include taking an action in response to receiving a user selection in response to the providing the brain atlas data and the indication of the degree of the connectivity metric between the seed parcel and the seed-connected parcel.

One or more embodiments described herein can include a method including obtaining connectivity data characterizing, for each pair of parcels comprising a first parcel and a second parcel from a group of parcels, a degree of correlation between a measure of brain activity of the first parcel and a measure of brain activity of the second parcel in a brain of a patient, identifying a seed parcel in brain atlas data associated with the brain of the patient, determining one or more other parcels in the group of parcels having a correlation metric with the seed parcel, the correlation metric satisfying a threshold correlation condition, and providing indications of correlations between the seed parcel and the one or more other parcels over the brain atlas data for presentation to the user.

In some implementations, the method can optionally include one or more of the following features. For example, the connectivity data can specify a connectivity matrix and each position in the connectivity matrix can characterize a pair of parcels, the method further including presenting the connectivity matrix in a portion of the GUI with the brain atlas data. The method can also include receiving user input indicating selection of one or more positions in the connectivity matrix, the positions being a column of the connectivity matrix or a row of the connectivity matrix, and identifying the seed parcel based on the user-selected one or more positions in the connectivity matrix. Providing indications of correlations between the seed parcel and the one or more other parcels over the brain atlas data for presentation to the user can include: providing data representing the GUI to a user device for displaying the GUI to the user, the interface including (i) a visual indication of the selected column or the selected row of the connectivity matrix and (ii) a visual representation of the brain atlas data. The seed parcel can be represented in a first indicia and the one or more other parcels can be represented in a second indicia, the second indicia being different than the first indicia.

As another example, the method can include providing, based on receiving the user input indicating selection of a parcel in the brain atlas data, a pop out window to be presented over a portion of the brain atlas data in the GUI, the pop out window including (i) a selectable option to export the selected parcel and (ii) information including a name or identifier associated with the selected parcel, receiving second user input indicating selection of the option to export the selected parcel, and generating a version of the brain atlas data with the selected parcel. The pop out window further can include a selectable option to identify the selected parcel as the seed parcel, the method further including: receiving user input indicating selection of the option to identify the selected parcel as the seed parcel, and identifying the seed parcel as the selected parcel.

In some implementations, the seed parcel can be represented in a first indicia, the first indicia being different than an indicia in which the one or more other parcels are represented. In some implementations, the method can also include providing a filtering slider to be presented in the GUI with the brain atlas data, receiving second user input indicating at least one adjustment to the filtering slider, the at least one adjustment including moving a first portion of the filtering slider closer to a left end of the filtering slider and moving a second portion of the filtering slider closer to a right end of the filtering slider, a third portion of the filtering slider between the first portion and the second portion representing correlations between the seed parcel and the one or more other parcels that are excluded from presentation over the brain atlas data, and providing indications of correlations between the seed parcel and a subset of the one or more other parcels where the correlations satisfy the at least one adjustment to the filtering slider, the indications of correlations being provided for presentation over the brain atlas data.

One or more embodiments described herein can include a system having one or more computers and one or more storage devices storing instructions that are operable, when executed by the one or more computers, to cause the one or more computers to perform operations including: obtaining connectivity data characterizing, for each pair of parcels comprising a first parcel and a second parcel from a group of parcels, a connectivity metric measuring a relationship between the first parcel and the second parcel in a brain of a patient, obtaining brain atlas data, identifying a seed parcel from the group of parcels, determining one or more other parcels in the group of parcels having a connectivity metric with the seed parcel that satisfies a threshold connectivity metric condition to provide at least one seed-connected parcel, and for the seed-connected parcel, providing the brain atlas data and an indication of a degree of the connectivity metric between the seed parcel and the seed-connected parcel for display to a user as an overlay on a visualization of the brain atlas data.

In some implementations, the system can optionally perform one or more of the above mentioned features.

The devices, systems, and techniques described herein may provide one or more of the following advantages. As discussed above, a set of brain data characterizing the brain of a single patient can often be incredibly large and complicated, and thus it can be difficult and time consuming for a user to extract useful information from the set of brain data. Using techniques described herein, a system can quickly determine, within seconds (e.g., with 600 seconds, within 200 seconds, with 100 seconds, within 60 seconds, within 30 seconds, within 20 seconds, within 10 seconds or within 5 seconds) and/or using minimal or little processing power, the subset of a brain atlas that is clinically relevant to a user and provide the determined subset for display to the user, so that the user is not forced to search through and analyze a large amount of data that is not clinically relevant. Therefore, the amount of time that a user must spend to discover the portion of the brain atlas that is useful to the user can be drastically reduced, resulting in improved outcomes for patients, users and/or clinicians, especially when effective care requires time sensitive investigations. Similarly, the disclosed technology can reduce complexity and dimensionality of the patient brain data for the relevant users to better understand the brain data through parcellation of the brain. The users can directly view information in relation to brain anatomy by visualizing the patient brain data in 2D and/or 3D space. The users can also interact directly with parcels of the patient's brain to perform tasks quickly and easily, such as making decisions about diagnoses, treatments, therapies (e.g., determining which therapy to give the patient and/or which therapy tends to improve the patient's condition over time, etc.), and other time sensitive investigations.

As a particular example, using existing systems it might take a user multiple hours to extract the subset of brain data of a patient required for a particular treatment, and because of the extensive time and attention required, the extracted subset can be inaccurate and error-prone. Using systems described herein, the process of extracting useful brain data from a corpus of brain data can be fully automated and executed in a matter of seconds or minutes and/or with minimal processing power.

Furthermore, the disclosed technology provides user-friendly and interactive GUI displays of functional MIll data in 3D and/or 2D space to ensure easy, efficient, and quick analysis of parcels of interest in the patient's brain. The disclosed GUI displays can use colors, patterns, and other uniform indicia to represent different parcels, seed parcel(s), and/or seed-connected parcels in the patient's brain data. Sensitivity to noise by prior brain imaging visualization systems can cause incorrect information, or information that the user does not wish to view, to be displayed in the existing brain data visualization schemes. The disclosed technology can provide intuitive and easy-to-use interactions between the user and the GUI displays such that the user can make simple, quick, and accurate selections of parcels to be viewed and analyzed in 2D and/or 3D space. The disclosed technology therefore provides efficient identification and derivation of connectivity metrics amongst parcels of interest in the patient's brain data (e.g., the seed parcel and seed-connected parcel(s)) that also uses minimal processing power and compute resources.

The details of one or more embodiments of the subject matter of this disclosure are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This document generally describes systems, methods, and techniques for identifying and visualizing functional patient brain data in logical parcels and in 2D and/or 3D space. The disclosed technology also provides intuitive, easy-to-use interactions between a relevant user and the visual displays of the brain data to facilitate accurate and efficient user-analysis and decision-making that relates to the patient's diagnosis, treatment, and/or therapy. Such interactions can include, but are not limited to, selecting a parcel as a seed parcel for which connectivity metrics are displayed between the seed parcel and other parcels in the brain data, selecting and exporting one or more target parcels, removing one or more parcels from view, and/or selecting or hovering over a parcel to identify the parcel's name and other information about the parcel. The user can also interact with the displayed brain data by filtering connectivity metrics shown between the seed parcel and seed-connected parcels, which can be beneficial for the user if they are wishing to focus on different brain data and/or diagnosis, treatment, and/or therapy related to particular conditions of the patient. One or more other visualizations of and interactions with the patient brain data are recognized, as described further below.

Figure 1A:
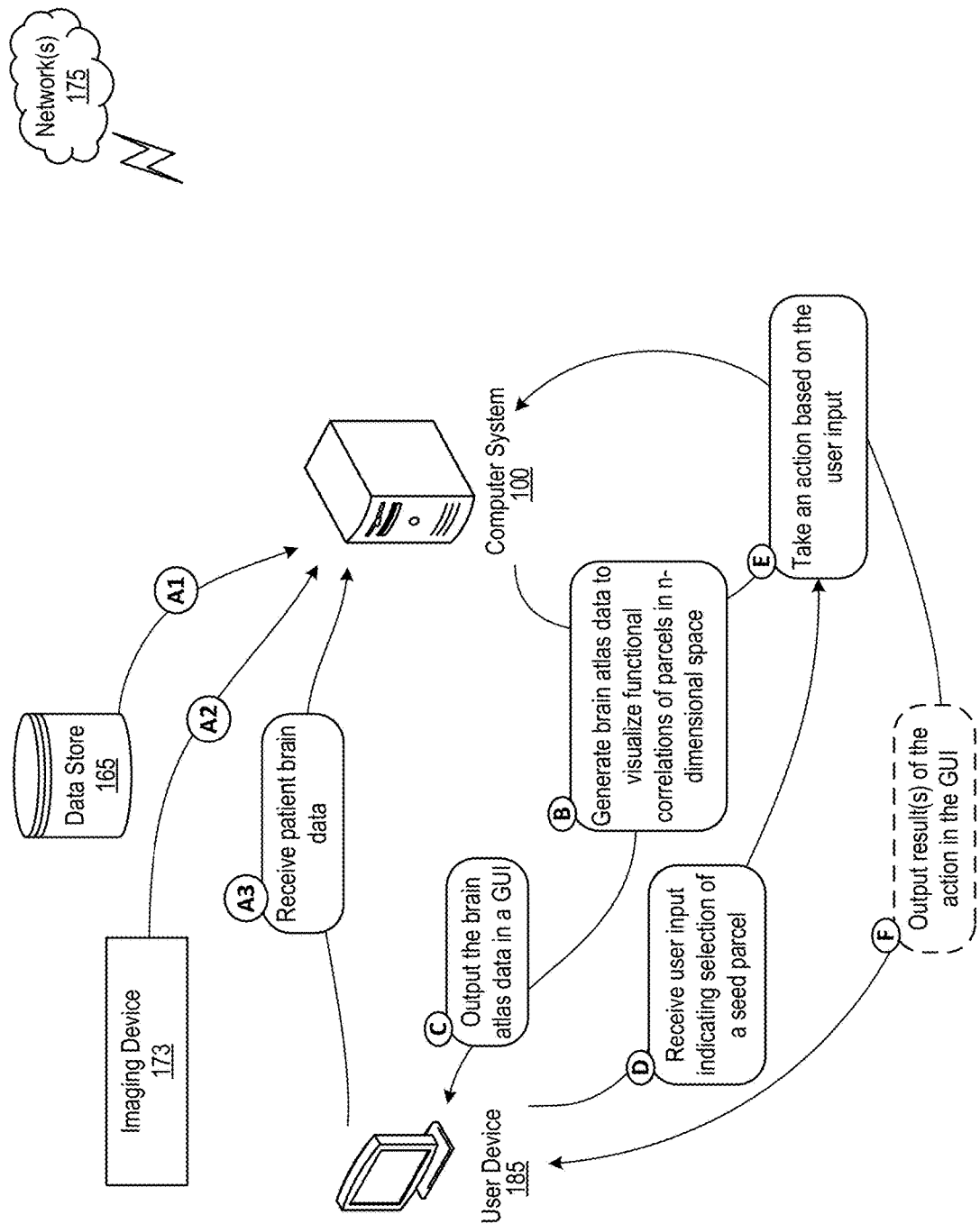
FIG. 1A is a conceptual diagram for visualizing connectivity metrics amongst parcels in patient brain data.

Referring to the figures, FIG. 1A is a conceptual diagram for visualizing connectivity metrics amongst parcels in patient brain data. A computer system 100 can be in communication (e.g., wired and/or wireless) with a data store 165, imaging device 173, and/or user device 185 via network(s) 175. In brief, the computer system 100 can be configured to process patient brain data and generate GUI displays that present information about the processed patient brain data, as described throughout this disclosure. The data store 165 can be configured to store patient brain data, connectivity metrics amongst parcels in the patient brain data, and other relevant patient data, brain data, diagnoses, treatments, and/or therapies (e.g., patient specific and/or general population). The imaging device 173 can be any type of medical imaging device that may be used by to capture brain data of the patient. For example, the imaging device 173 can be, but is not limited to, a magnetic resonance imaging (MRI) system, a functional MRI (fMRI) system, a positron emission tomography (PET) system, a near infrared spectroscopy (NIRS) system, a magnetoencephalogram (MEG) system, and/or an electroencephalography (EEG) system. The user device 185 can be used by a relevant user, such as a clinician, physician, surgeon, or other medical professional. The relevant user can view visualizations of parcels in the patient brain data at the user device 185. The relevant user can also interact with these visualizations at the user device 185, as described herein. As shown in FIG. 1A, the user device 185 can be separate from the computer system 100. The user device 185 can be part of the computer system 100, in some implementations.

Figure 1B:
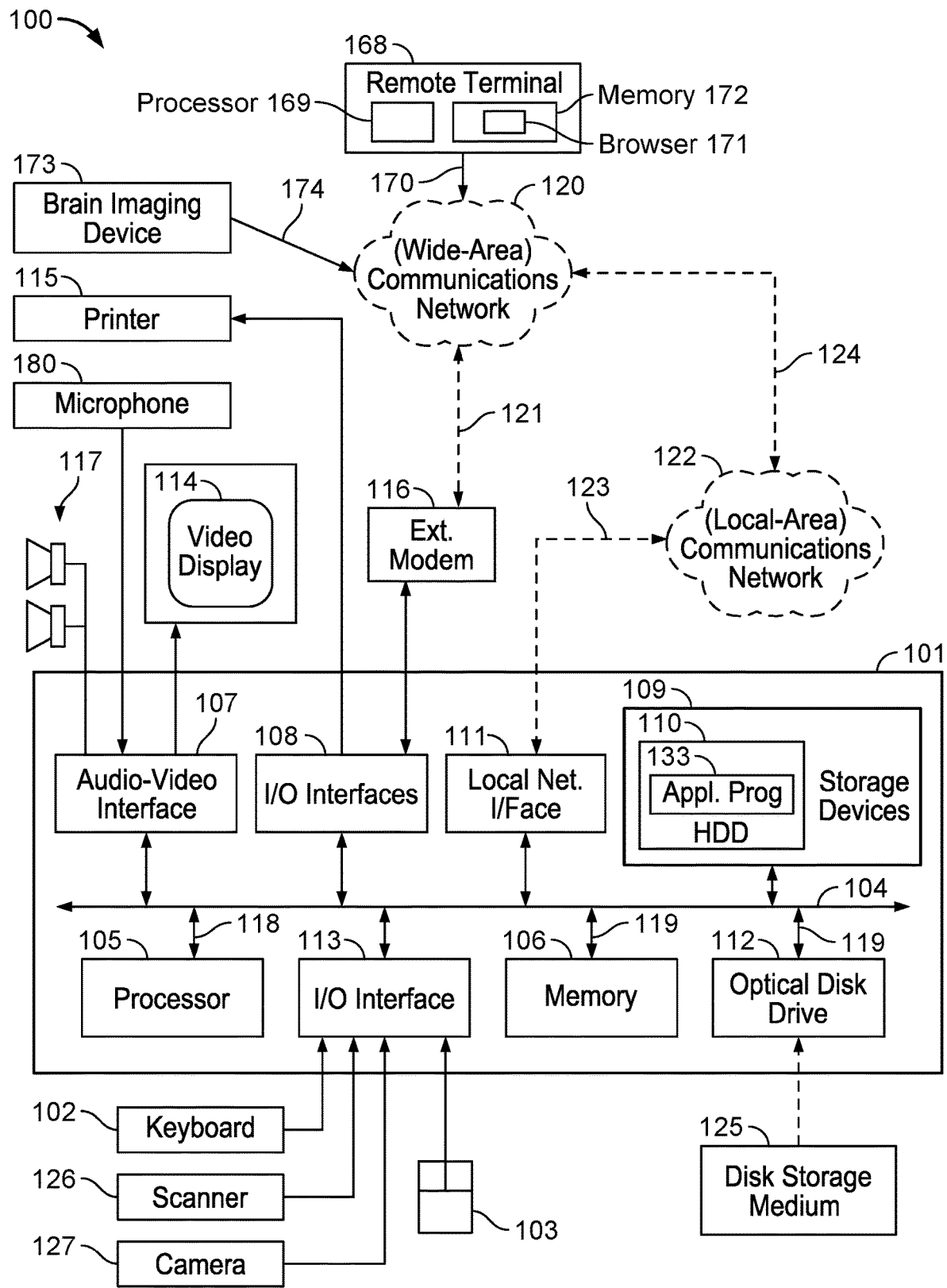
FIG. 1B and FIG. 1C are block diagrams that illustrate an example computer system for use in processing medical images.
Figure 1C:
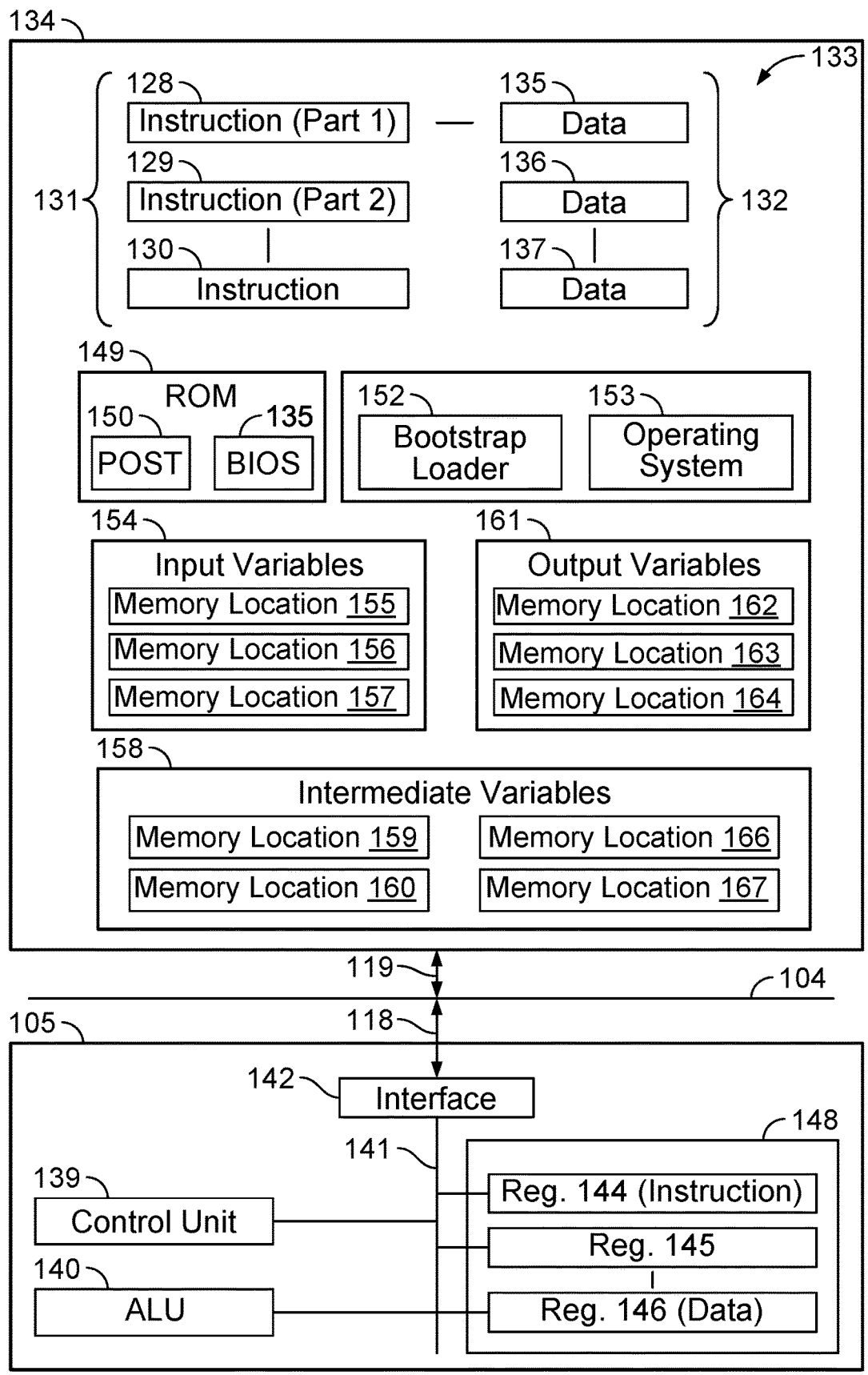

The computer system 100 is described in further detail in reference to FIGS. 1B-C. The data store 165 is described in further detail in reference to data store 210 in FIGS. 2A-B.

Figure 2A:
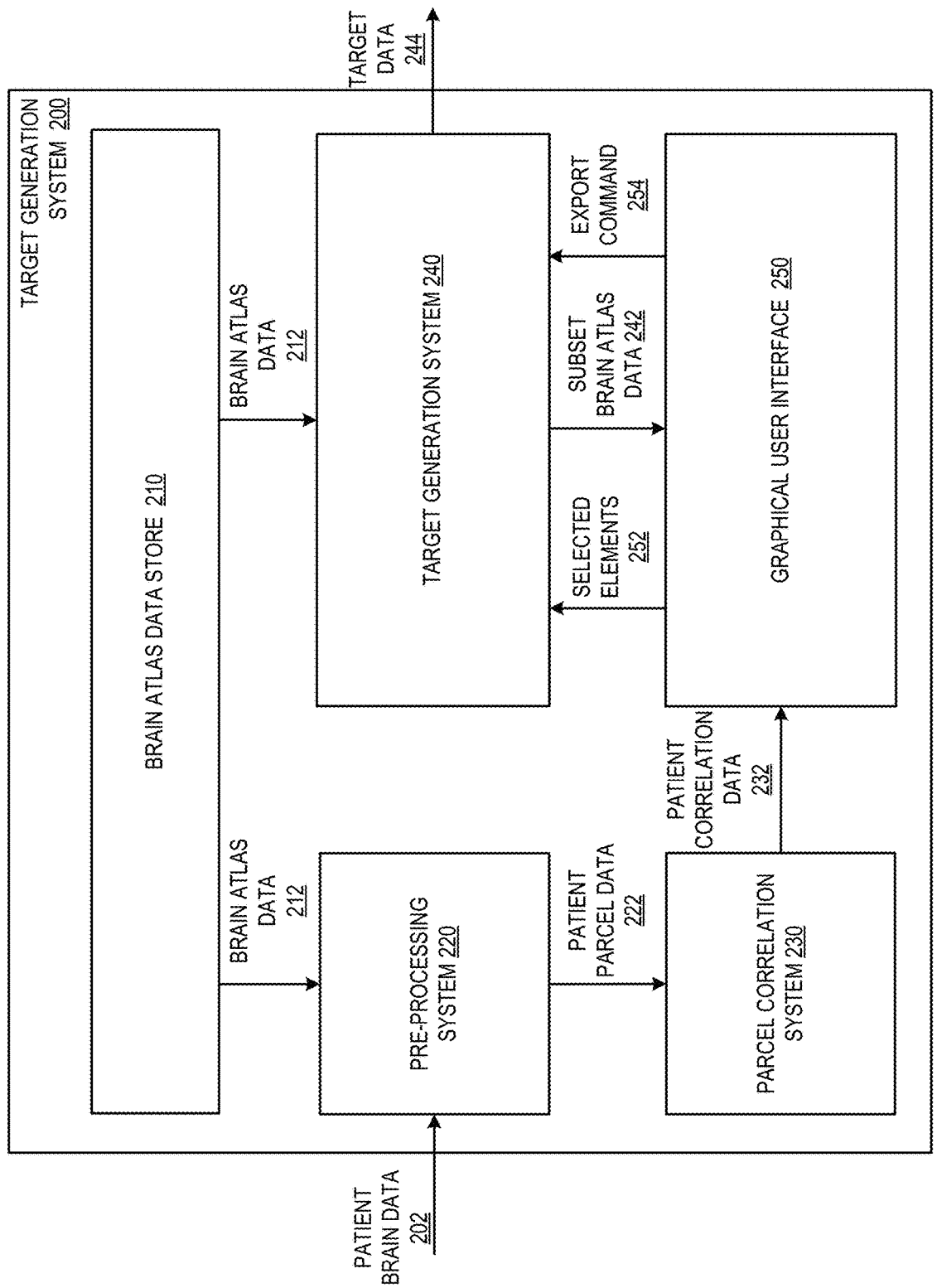
FIG. 2A and FIG. 2B are diagrams of an example target generation system.
Figure 2B:
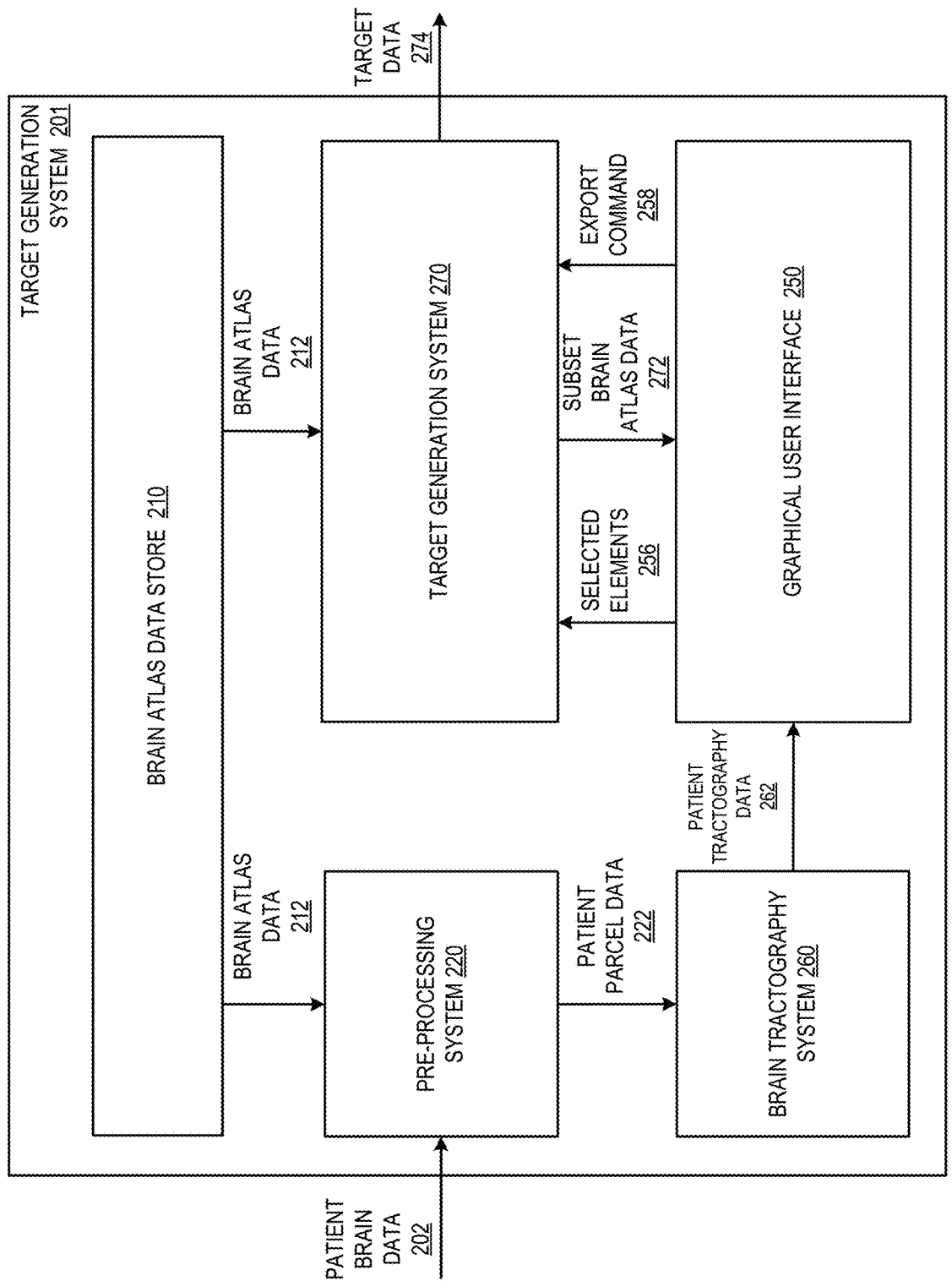

The user device 185 is described in further detail in reference to GUI 250 in FIGS. 2A-B. Moreover, the network(s) 175 is described in further detail in reference to wide area network 120 and/or local communications network 122 in FIG. 1B.

Still referring to FIG. 1A, the computer system 100 can receive patient brain data from the data store 165 (block A1), the imaging device 173 (block A2), and/or the user device 185 (block A3). For example, brain image data can be captured by the imaging device 173 then stored in the data store 165. The computer system 100 can then retrieve the brain image data from the data store 165 in block A1 at another time (e.g., when the relevant user is ready to analyze the patient's brain data). As another example, the imaging device 173 can capture the brain image data and transmit the data directly to the computer system 100 in block A2, in real-time or near real-time. As yet another example, the relevant user can select patient brain data at the user device 185 and the user device 185 can transmit that selection to the computer system 100 in block A3. The user selection of patient brain data can be performed when the relevant user is analyzing the patient's brain to diagnose the patient's condition and/or determine an appropriate treatment and/or therapy.

The computer system 100 can generate brain atlas data to visualize functional correlations of parcels in n-dimensional space using the patient brain data (block B). For example, as shown and described in FIGS. 3A-F, the computer system 100 can identify parcels in the patient brain data and depict the parcels overlaid over portions of the brain atlas data. The parcels can be represented in one or more indicia, such as colors, highlighting, and/or patterns, to provide for easy visualization of those parcels relative to each other. The computer system 100 can also visually represent the parcels in n-dimensional space to show connectivity metrics amongst one or more parcels. For example, the computer system 100 can select a seed parcel (such as a default seed parcel, which the user can then change by interacting with the GUI displays presented at the user device 185), identify parcels having a connectivity relationship with the seed parcel, and visually depict the seed parcel and the identified parcels overlaying the brain atlas data. Moreover, n-dimensional space can include 2D space and/or 3D space. In some implementations, for example, the user can toggle between a 2D view of the brain atlas data with the functional correlations of parcels and a 3D view of the brain atlas data with the functional correlations of parcels. Depicting such information in 2D and/or 3D space can be beneficial to distill complex brain information in a digestible format for quick, accurate, and easy analysis by the relevant user.

The computer system 100 can transmit the brain atlas data to the user device 185 to be outputted in a GUI display (block C). For example, the brain atlas data can be presented in 2D and/or 3D space with a connectivity matrix for a network of parcels in the brain data of the patient. Refer to FIGS. 3A-F for additional discussion about the GUI display.

The relevant user can interact with the data presented in the GUI display at the user device 185, as described herein. Accordingly, the computer system 100 can receive user input indicating selection of a seed parcel in block D. As described herein, the user can select the seed parcel directly from the 2D and/or 3D visualization of the brain atlas data by clicking or tapping on a parcel of interest. The user can also select the seed parcel from the connectivity matrix that may be presented in the GUI display with the 2D and/or 3D visualization of the brain atlas data (e.g., the user can select a column and/or a row in the connectivity matrix). The seed parcel can be a parcel of importance or a target parcel related to the user's analysis of the patient's condition(s).

In some implementations, the user can provide one or more other inputs at the user device 185, which can be received by the computer system 100 in block D. For example, the user can select a target parcel to be exported. As another example, the user can select a parcel to be removed from the current visualization of the brain atlas data. As yet another example, the user can select and/or hover over a parcel to view an identifier or name of the parcel. The user can also select and/or hover over a parcel to view additional information about that parcel, which can be used by the user in analyzing the patient's condition(s). Additionally, the user can toggle one or more sliders and/or filters in a legend presented in the GUI display to view different brain data, different connectivity metrics, and/or varying degrees of connectivity amongst parcels in the visualized brain atlas data.

Once the computer system 100 receives the user input in block D, the computer system 100 can take an action based on the user input (block E). For example, if the user input indicates user selection of a parcel to be the seed parcel, the computer system 100 can update the visualization of the brain atlas data by depicting the new seed parcel in an indicia, such as a color (e.g., green), that indicates the parcel is the seed parcel. The computer system 100 can also identify other parcels having connectivity relationships with the seed parcel and display such relationships (and/or the other parcels) in the visualization of the brain atlas data. The connectivity relationships can be defined as tracts connecting the parcels, electrical activity between the parcels, and/or anomalous correlations of electrical activity between the parcels. One or more other connectivity relationships can be realized and used to identify seed-connected parcels in block E. Thus, the computer system 100 can use the user-selected seed parcel to find all other parcels in the brain data having connects to the seed parcel (e.g., meeting some threshold condition(s) or connectivity metric conditions to have a relationship with the seed parcel). Refer to FIGS. 3A-F for additional discussion about computer system 100 actions in response to the user input.

Optionally, the computer system 100 can output one or more results of the actions taken in block E in the GUI presented at the user device 185 (block F). For example, as mentioned above, the computer system 100 can update the GUI to include the seed parcel in the indicia and to visually depict the parcels having connectivity relationships with the seed parcel in the visualization of the brain atlas data. In some implementations, the parcels having the connectivity relationships with the seed parcel can be depicted in another indicia, such as a color. The another indicia can be different than the indicia of the seed parcel. In some implementations, the another indicia can be the same as the indicia of the seed parcel. Refer to FIGS. 3A-F for additional discussion about outputting the results of the actions performed by the computer system 100.

FIGS. 1B and 1C are block diagrams of a general-purpose computer system 100 upon which one can practice arrangements described herein. The following description is directed primarily to a computer server module 101. However, the description applies equally or equivalently to one or more remote terminals 168.

As seen in FIG. 1B, the computer system 100 can include the server computer module 101; input devices such as a keyboard 102, a pointer device 103 (e.g., a mouse), a scanner 126, a camera 127, and a microphone 180; and output devices including a printer 115, a display device 114 and loudspeakers 117. An external Modulator-Demodulator (Modem) transceiver device 116 may be used by the computer server module 101 for communicating to and from the remote terminal 168 over a computer communications network 120 via a connection 121 and a connection 170. The aforementioned communication can take place between the remote terminal 168 and "the cloud" which in the present description comprises at least the one server module 101. The remote terminal 168 typically has input and output devices (not shown) which are similar to those described in regard to the server module 101. The communications network 120 may be a wide-area network (WAN), such as the Internet, a cellular telecommunications network, or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer server module 101 typically includes at least one processor unit 105, and a memory unit 106. For example, the memory unit 106 may have semiconductor random access memory (RAM) and semiconductor read only memory (ROM). The remote terminal 168 typically includes as least one processor 169 and a memory 172. The computer server module 101 also includes a number of input/output (I/O) interfaces including: an audio-video interface 107 that couples to the video display 114, loudspeakers 117 and microphone 180; an I/O interface 113 that couples to the keyboard 102, mouse 103, scanner 126, camera 127 and optionally a joystick or other human interface device (not illustrated); and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1B, the local communications network 122 may also couple to the wide network 120 via a connection 124, which would typically include a so-called "firewall" device or device of similar functionality. The local network interface 111 may include an Ethernet circuit card, a Bluetooth® wireless arrangement or an IEEE 802.11 wireless arrangement; however, numerous other types of interfaces may be practiced for the interface 111.

The I/O interfaces 108 and 113 may afford either or both of serial or parallel connectivity; the former may be implemented according to the Universal Serial Bus (USB) standards and having corresponding USB connectors (not illustrated). Storage memory devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119.

The techniques described herein may be implemented using the computer system 100, e.g., may be implemented as one or more software application programs 133 executable within the computer system 100. In some implementations, the one or more software application programs 133 execute on the computer server module 101 (the remote terminal 168 may also perform processing jointly with the computer server module 101), and a browser 171 executes on the processor 169 in the remote terminal, thereby enabling a user of the remote terminal 168 to access the software application programs 133 executing on the server 101 (which is often referred to as "the cloud") using the browser 171. In particular, the techniques described herein may be effected by instructions 131 (see FIG. 1C) in the software 133 that are carried out within the computer system 100. The software instructions 131 may be formed as one or more code modules, each for performing one or more particular tasks. The software may also be divided into two separate parts, in which a first part and the corresponding code modules performs the described techniques and a second part and the corresponding code modules manage a user interface between the first part and the user.

The software may be stored in a computer readable medium, including the storage devices described below, for example. The software is loaded into the computer system 100 from the computer readable medium, and then executed by the computer system 100. A computer readable medium having such software or computer program recorded on the computer readable medium is a computer program product. Software modules for that execute techniques described herein may also be distributed using a Web browser.

The software 133 is typically stored in the HDD 110 or the memory 106 (and possibly at least to some extent in the memory 172 of the remote terminal 168). The software is loaded into the computer system 100 from a computer readable medium, and executed by the computer system 100. Thus, for example, the software 133, which can include one or more programs, may be stored on an optically readable disk storage medium (e.g., CD-ROM) 125 that is read by the optical disk drive 112. A computer readable medium having such software or computer program recorded on it is a computer program product.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any non-transitory tangible storage medium that provides recorded instructions and/or data to the computer system 100 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. For example, through manipulation of the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1C is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1B.

When the computer module 101 is initially powered up, a power-on self-test (POST) program 150 can execute. The POST program 150 can be stored in a ROM 149 of the semiconductor memory 106 of FIG. 1B. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 can activate the hard disk drive 110 of FIG. 1B. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfil various high-level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1B must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1C, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119.

The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively. Depending upon the relative size of the instructions 131 and the memory locations 128-130, a particular instruction may be stored in a single memory location as depicted by the instruction shown in the memory location 130. Alternately, an instruction may be segmented into a number of parts each of which is stored in a separate memory location, as depicted by the instruction segments shown in the memory locations 128 and 129.

In general, the processor 105 is given a set of instructions which are executed therein. The processor 105 waits for a subsequent input, to which the processor 105 reacts to by executing another set of instructions. Each input may be provided from one or more of a number of sources, including data generated by one or more of the input devices 102, 103, data received from an external source 173, e.g., a brain imaging device 173 such as an MII or DTI scanner, across one of the networks 120, 122, data retrieved from one of the storage devices 106, 109 or data retrieved from a storage medium 125 inserted into the corresponding reader 112, all depicted in FIG. 1B. The execution of a set of the instructions may in some cases result in output of data. Execution may also involve storing data or variables to the memory 134.

Some techniques described herein use input variables 154, e.g., data sets characterizing the brain of a patient, which are stored in the memory 134 in corresponding memory locations 155, 156, 157. The techniques can produce output variables 161, which are stored in the memory 134 in corresponding memory locations 162, 163, 164. Intermediate variables 158 may be stored in memory locations 159, 160, 166 and 167.

Referring to the processor 105 of FIG. 1C, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle can include i) a fetch operation, which fetches or reads an instruction 131 from a memory location 128, 129, 130; ii) a decode operation in which the control unit 139 determines which instruction has been fetched; and iii) an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 132.

Each step or sub-process in the techniques described herein may be associated with one or more segments of the program 133 and is performed by the register section 144, 145, 146, the ALU 140, and the control unit 139 in the processor 105 working together to perform the fetch, decode, and execute cycles for every instruction in the instruction set for the noted segments of the program 133. Although a cloud-based platform has been described for practicing the techniques described herein, other platform configurations can also be used. Furthermore, other hardware/software configurations and distributions can also be used for practicing the techniques described herein.

FIGS. 2A and 2B are diagrams of example target generation systems 200 and 201, respectively. The target generation systems 200 and 201 are examples of systems implemented as computer programs on one or more computers in one or more locations, in which the systems, components, and techniques described below can be implemented. As depicted in FIG. 2A, the target generation system 200 is configured to determine a subset of brain atlas data according to a user selection of one or more particular elements of patent correlation data. As depicted in FIG. 2B, the target generation system 200 is configured to determine a subset of brain atlas data according to a user selection of one or more particular elements of patient tractography data.

Referring to FIG. 2A, the target generation system 200 is configured to obtain patient brain data 202 characterizing the brain of a patient and process the patient brain data 202 to generate target data 244. For example, the patient brain data 202 can include one or more of blood-oxygen-level-dependent imaging data, fMRI data, or EEG data captured from the brain of the patient.

The target generation system 200 includes a brain atlas data store 210, a pre-processing system 220, a parcel correlation system 230, a target generation system 240, and a graphical user interface 250.

In some implementations, the target generation system 200 is local to the user, e.g., a component of a user device. In some other implementations, one or more components of the target generation system 200 are non-local to the user, e.g., hosted within a data center, which can be a distributed computing system having hundreds or thousands of computers in one or more locations. As a particular example, the graphical user interface 250 might be local to the user, while each of the other components of the target generation system 200 are on the cloud and communicatively connected to the graphical user interface 250.

The brain atlas data store 210 is configured to maintain brain atlas data 212, which defines multiple parcels of the human brain. For example, the brain atlas data 212 can include a model of the brain composed of three-dimensional voxels, where each voxel is defined by a location and orientation in a common coordinate system of the brain. Each voxel can be assigned to a particular parcel, so that the location and shape of each parcel is defined by the respective voxels assigned to the parcel. As a particular example, the brain atlas data 212 can be stored using a tabular format that maps (x,y,z) locations within the brain to an identification of a particular parcel. As another particular example, the brain atlas data 212 can be stored in a document-oriented database, e.g., using a JSON model. As another particular example, the brain atlas data 212 can be stored using a collection of three-dimensional tensors that identify, for respective (x,y,z) locations within the brain, a particular parcel.

The pre-processing system 220 is configured to obtain the patient brain data 202 and process the patient brain data 202 to generate patient parcel data 222 which organizes the patient brain data 202 according to multiple different parcels of the brain of the patient. The pre-processing system 220 can generate the patient parcel data 222 according to the brain atlas data 212, obtained from the brain atlas data store 210.

For example, the patient brain data 202 can include multiple different time series characterizing the activity of a respective different region of the brain of the patient over time, e.g., a respective time series corresponding to each three-dimensional voxel of the brain that can be measured by an MM machine. The pre-processing system 220 can organize the different time series signals by parcel according to a brain atlas of the brain. For example, for each voxel in the brain data 202, the pre-processing system 220 can determine the parcel to which the corresponding voxel in the brain atlas data 212 is assigned. The pre-processing system 220 can then, for each parcel, combine the different time series signals corresponding to the parcel, e.g., by determining an average of the different time series signals.

In some implementations the pre-processing system 220 performs one or more additional pre-processing steps to generate the patient parcel data 222. For example, the pre-processing system 220 can perform smoothing on the patient brain data 202, e.g., to remove components of the patient brain data 202 that are not clinically relevant such as brain activity data related to the heartbeat or breathing of the patient. As another example, the pre-processing system 220 can perform skull stripping on the patient brain data 202. As another example, the pre-processing system 220 can remove one or more slices in brain data 202 in order to allow for signal stabilization. As another example, the pre-processing system 220 can perform slice timing correction on the brain data 202. As another example, the pre-processing system 220 can perform motion correction on the brain data 202. As another example, the pre-processing system 220 can perform gradient distortion correction on the brain data 202. As another example, the pre-processing system 220 can perform global intensity normalization on the brain data 202. As another example, the pre-processing system 220 can calculate one or more confounds using the brain data 202. As another example, the pre-processing system 220 can apply a whitening transform to the brain data 202.

The parcel correlation system 230 is configured to obtain the patient parcel data 222 and to process the patient parcel data 222 to generate patient correlation data 232 that characterizes, for each pair of parcels of the multiple parcels in the patient parcel data 222, a correlation between brain activity of the first parcel and brain activity of the second parcel in the brain of the patient.

For example, the patient parcel data 222 can include one or more time series signals corresponding to each parcel, and the parcel correlation system 230 can determine, for each pair of parcels, a correlation between the values of the time series of the first parcel and the time series of the second parcel.

In some implementations, the parcel correlation system 230 processes the patient parcel data to generate a connectivity matrix for display to the user. A connectivity matrix can be generated from the brain functional connectivity data of a patient, and displays the correlation between areas of the brain of the patient. In particular, for an element of a connectivity matrix in a row that corresponds to a first parcel of the brain and in a column that corresponds to a second parcel of the brain, the value of the element characterizes the correlation between the first parcel and the second parcel.

In some implementations, the parcel correlation system 230 determines one or more pairs of parcels whose correlation is anomalous. For example, the parcel correlation system 230 can obtain normal correlation data that identifies, for each pair of parcels in the patient parcel data 222, a range of values for the correlation between the pair of parcels that is considered "normal." The normal range can be determined according to the correlation between the pair of parcels measured in the respective brain of multiple other patients. For example, the normal correlation data can be determined from brain data captured from hundreds, thousands, or millions of other patients. As a particular example, the normal correlation data might identify, for each pair of parcels, an average correlation between the pair of parcels and a standard deviation of correlations between the pair of parcels, as determined from the correlations measured in the brains of the other patients. Using the normal correlation data, the parcel correlation system 230 can determine one or more pairs of parcels in the patient parcel data 222 whose correlation is anomalous, and identify the one or more determined pairs of parcels in the patient correlation data 232.

In some implementations, the parcel correlation system 230 generates an anomaly correlation matrix for display to the user. As described herein, an anomaly correlation matrix is a connectivity matrix that visually identifies one or more pairs of parcels, corresponding to respective elements in the anomaly correlation matrix, whose correlation has been determined to be anomalous.

The graphical user interface 250 is configured to obtain the patient correlation data 232 and display data characterizing the patient correlation data 232 to the user. For example, the graphical user interface 250 can display a list of the correlation between each pair of parcels. As another example, the graphical user interface 250 can display a list of one or more pairs of parcels whose correlation the parcel correlation system 230 has determined to be anomalous. As another example, the graphical user interface 250 can display a connectivity matrix or anomaly correlation matrix characterizing the correlation between respective pairs of parcels in the brain of the patient. As another example, the graphical user interface 250 can display a text summary of the pairs of parcels whose correlation the parcel correlation system 230 has determined to be anomalous. As another example, the graphical user interface 250 can display a score calculated by the parcel correlation system 230 that characterizes a degree of anomaly in the brain of the patient, e.g., a value between 0 and 1.

In some implementations, the graphical user interface 250 can also display one or more components of the patient brain data 202 to the user. For example, the graphical user interface 250 might display brain image data, e.g, MRI images of the brain of the user.

The graphical user interface 250 is configured to receive a user input identifying one or more particular elements 252 of the patient correlation data. The selected elements 252 can include any subset of the patient correlation data 232. For example, the selected elements 252 of the patient correlation data can include a particular pair of parcels, a particular parcel, a group of pairs of parcels, and/or a group of parcels (e.g., each parcel associated with the language region of the brain). The user can select the one or more particular elements 252 using any appropriate user input device, e.g., the pointer device 103, or the microphone 180 depicted in FIG. 1B. As a particular example, the user can select a particular row or column of the matrix or the anomaly correlation matrix.

The graphical user interface 250 can provide the selected elements 252 to the target generation system 240. The target generation system 240 is configured to process the selected elements 252 to determine a set of one or more particular parcels associated with the selected elements 252. For example, if the selected elements 252 identify one or more pairs of parcels, the target generation system 240 can determine the set of parcels to include each parcel included in the one or more pairs of parcels.

The target generation system 240 can obtain the brain atlas data 212 from the brain atlas data store 210, and use the brain atlas data 212 to generate a subset 242 of the brain atlas data that corresponds to the determined set of parcels. That is, the determined subset 242 of the brain atlas data characterizes the location and shape of the parcels in the determined set of parcels. For example, the subset 242 of brain atlas data can identify each three-dimensional voxel in the brain atlas data 212 that is assigned to a parcel in the determined set of parcels.

The graphical user interface 250 can receive the subset 242 of the brain atlas data and render the subset 242 for the user. For example, the graphical user interface 250 can display a three-dimensional model of the parcels characterized by the subset 242 of the brain atlas data. That is, the graphical user interface 250 can display to the user a model of the parcels corresponding to the elements 252 that were selected by the user.

The graphical user interface 250 can receive a user input characterizing an export command 254 to export the subset 242 of the brain atlas data. The user can provide the export command 254 using any appropriate user input device, e.g., the pointer device 103, or the microphone 180 depicted in FIG. 1B. The graphical user interface 250 can then provide the export command 254 to the target generation system 240.

In response to receiving the export command 254, the target generation system 240 can generate target data 244 that characterizes the subset 242 of the brain atlas data. The target generation system 240 can then export the target data 244 to an external system. For example, the target generation system 240 can provide the target data 244 to an external device for delivering a treatment to the patient, e.g., an image guidance system for delivering a TMS treatment to the patient, and/or an external user system for further analysis by the user.

In some implementations, the target generation system 240 generates and exports the target data 244 when the target generation system 240 receives the selected elements 252. That is, the export command 254 can be included in the data sent to the target generation system 240 characterizing the selected elements 252, so that the target generation system 240 does not send the subset 242 of the brain atlas data 242 to the graphical user interface 250 for display to the user, but rather immediately generates and exports the target data 244.

Referring to FIG. 2B, the target generation system 201 is configured to obtain patient brain data 202 characterizing the brain of a patient and process the patient brain data 202 to generate target data 274. For example, the patient brain data 202 can include one or more of blood-oxygen-level-dependent imaging data, fMRI data, or EEG data captured from the brain of the patient.

The target generation system 200 includes a brain atlas data store 210, a pre-processing system 220, a brain tractography system 260, a target generation system 270, and a graphical user interface 250.

As described above with reference to FIG. 2A, in some implementations, the target generation system 201 is local to the user, e.g., a component of a user device. In some other implementations, one or more components of the target generation system 200 are non-local to the user, e.g., hosted within a data center, which can be a distributed computing system having hundreds or thousands of computers in one or more locations.

The brain atlas data store 210 is configured to maintain brain atlas data 212, which defines multiple parcels of the human brain.

The pre-processing system 220 is configured to obtain the patient brain data 202 and process the patient brain data 202 to generate patient parcel data 222 which organizes the patient brain data 202 according to multiple different parcels of the brain of the patient. The pre-processing system 220 can generate the patient parcel data 222 according to the brain atlas data 212, obtained from the brain atlas data store 210. As described above with reference to FIG. 2A, in some implementations the pre-processing system 220 performs one or more additional pre-processing steps to generate the patient parcel data 222.

The brain tractography system 260 is configured to obtain the patient parcel data 222 and to process the patient parcel data 222 to generate patient tractography data 262 that characterizes, for each pair of parcels of multiple parcels in the patient parcel data 222, neural tracts connecting the pair of parcels in the brain of the patient.

In some implementations, the brain tractography system 260 determines one or more pairs of parcels for which the number of connections in the patient tractography data 262 is anomalous. For example, the brain tractography system 260 can obtain normal tractography data that identifies, for each pair of parcels in the patient parcel data 222, a range of values for the number of tracts connecting the pair of parcels that is considered "normal." The normal range can be determined according to the number of tracts connecting the pair of parcels measured in the respective brains of multiple other patients. For example, the normal tractography data can be determined from brain data captured from hundreds, thousands, or millions of other patients. As a particular example, the normal tractography data might identify, for each pair of parcels, an average number of tracts between the pair of parcels and a standard deviation of the number of tracts between the pair of parcels, as determined from the neural tracts measured in the brains of the other patients. Using the normal tractography data, the brain tractography system 260 can determine one or more pairs of parcels in the patient parcel data 222 for which the number of tracts connecting the pair of parcels is anomalous, and identify the one or more determined pairs of parcels in the patient tractography data 262.

The graphical user interface 250 is configured to obtain the patient tractography data 262 and display data characterizing the patient tractography data 262 to the user. For example, the graphical user interface 250 can display a list of the number of tracts between each pair of parcels. As another example, the graphical user interface 250 can display a list of one or more pairs of parcels whose number of connecting tracts the brain tractography system 260 has determined to be anomalous. As another example, the graphical user interface 250 can display a matrix characterizing the number of tracts connecting respective pairs of parcels in the brain of the patient. As another example, the graphical user interface 250 can display a text summary of the pairs of parcels whose number of connecting tracts the brain tractography system 260 has determined to be anomalous. As another example, the graphical user interface 250 can display a score calculated by the tractography system 260 that characterizes a degree of anomaly in the brain of the patient, e.g., a value between 0 and 1.

In some implementations, the graphical user interface 250 can also display one or more components of the patient brain data 202 to the user. For example, the graphical user interface 250 might display brain image data, e.g, MRI images of the brain of the user.

The graphical user interface 250 is configured to receive a user input identifying one or more particular elements 256 of the patient tractography data 262. The selected elements 256 can include any subset of the patient tractography data 262. For example, the selected elements 256 of the patient tractography data 262 can include a particular pair of parcels, a particular parcel, a group of pairs of parcels, and/or a group of parcels (e.g., each parcel associated with the language region of the brain).

The graphical user interface 250 can provide the selected elements 256 to the target generation system 270. The target generation system 270 is configured to process the selected elements 256 to determine a set of one or more particular parcels associated with the selected elements 256. For example, if the selected elements 256 identify one or more pairs of parcels, the target generation system 270 can determine the set of parcels to include each parcel included in the one or more pairs of parcels.

The target generation system 270 can obtain the brain atlas data 212 from the brain atlas data store 210, and use the brain atlas data 212 to generate a subset 272 of the brain atlas data that corresponds to the determined set of parcels. That is, the determined subset 272 of the brain atlas data characterizes the location and shape of the parcels in the determined set of parcels. For example, the subset 272 of brain atlas data can identify each three-dimensional voxel in the brain atlas data 212 that is assigned to a parcel in the determined set of parcels.

The graphical user interface 250 can receive the subset 272 of the brain atlas data and render the subset 272 for the user. For example, the graphical user interface 250 can display a three-dimensional model of the parcels characterized by the subset 272 of the brain atlas data. That is, the graphical user interface 250 can display to the user a model of the parcels corresponding to the elements 256 that were selected by the user.

The graphical user interface 250 can receive a user input characterizing an export command 258 to export the subset 272 of the brain atlas data. The graphical user interface 250 can then provide the export command 258 to the target generation system 270.

In response to receiving the export command 258, the target generation system 270 can generate target data 274 that characterizes the subset 272 of the brain atlas data. The target generation system 270 can then export the target data 274 to an external system, as described above with reference to FIG. 2A.

In some implementations, the target generation system 270 generates and exports the target data 274 when the target generation system 270 receives the selected elements 256. That is, the export command 258 can be included in the data sent to the target generation system 270 characterizing the selected elements 256, so that the target generation system 270 does not send the subset 272 of the brain atlas data 272 to the graphical user interface 250 for display to the user, but rather immediately generates and exports the target data 274.

Refer to FIGS. 3A-F described below for additional discussion about the graphical user interface 250 and the techniques described in reference to FIGS. 2A-B.

Figure 3A:
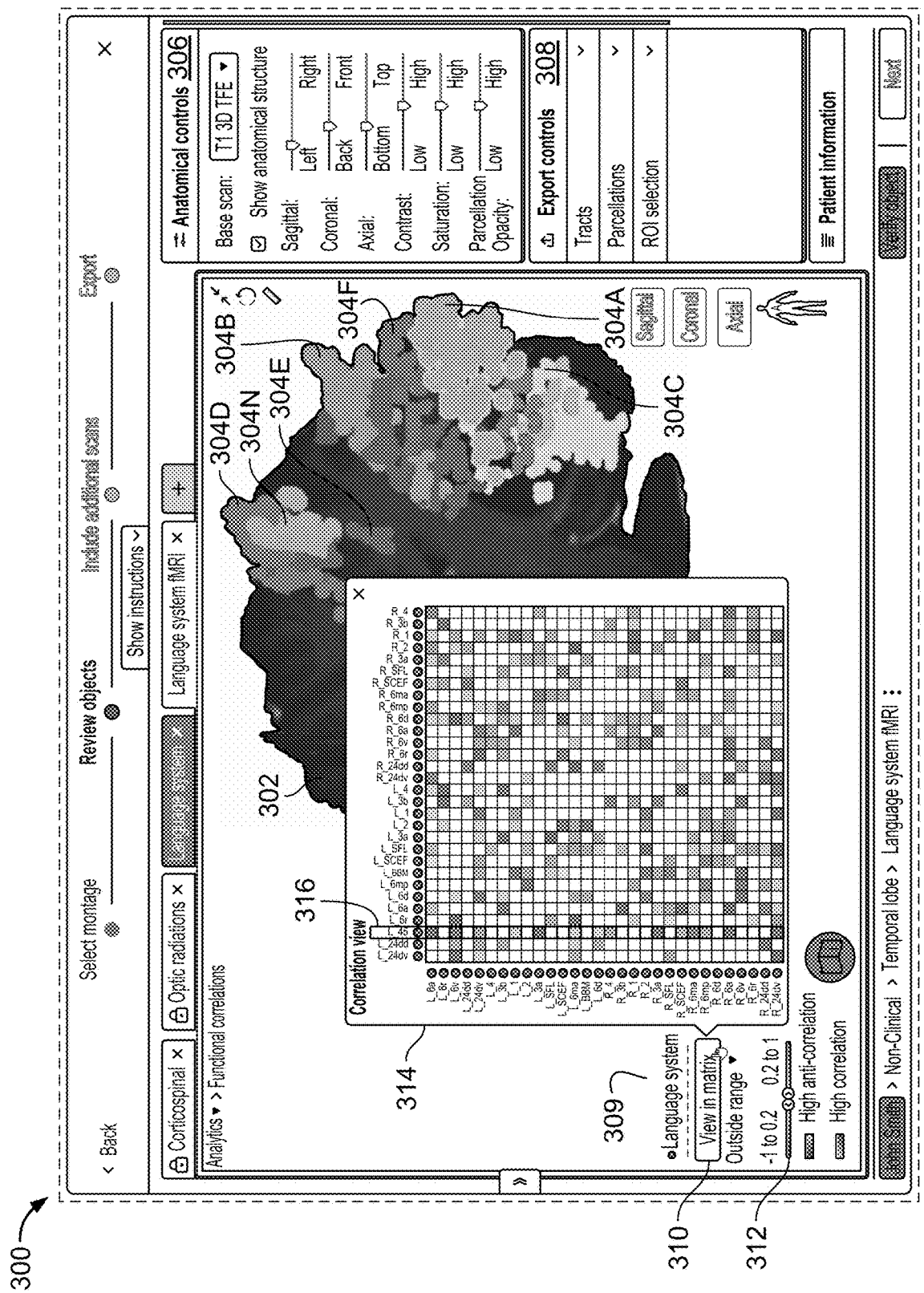
FIG. 3A illustrates an example graphical user interface (GUI) display for viewing a seed parcel and an example connectivity matrix in 3D space.

FIG. 3A illustrates an example graphical user interface (GUI) 300 display for viewing a seed parcel 304A and an example connectivity matrix 314 in 3D space. The GUI 300 can include brain atlas data 302. The brain atlas data 302 is a 3D representation of a patient's brain. In some implementations, the brain atlas data 302 can be represented in 2D space, as described in reference to FIG. 3F. To load the GUI 300, the user can select which types of parcels (e.g., which network) to view overlaying the brain atlas data 302. As an example, the user can select an option to view parcels associated with a motor network. Therefore, only motor parcels may be shown overlaying the brain atlas data 302 and in the matrix 314.

Parcels 304A-N are represented in one or more indicia (e.g., colors, patterns, etc.) and overlaying portions of the brain atlas data 302 that correspond to parcels in a particular patient's brain data. The brain atlas data 302 can include multiple voxels each assigned to a particular parcel 304A-N. The parcels 304A-N shown in FIG. 3A can have some degree of connectivity/correlation with a seed parcel, such as the selected seed parcel 304A. The seed parcel 304A can be a parcel to which all other parcels are benchmarked. There can be a default seed parcel for each network, such as language, motor, and/or vision. The user can then adjust which parcel is the seed parcel by selecting a different parcel, as described further in reference to FIGS. 3A-F. In some implementations, the user can also select a parcel to be the seed parcel from a list of preferred parcels per network. Other parcels that satisfy correlation thresholds (or other connectivity metric threshold) can then be presented in another indicia overlaying the brain atlas data 302 and in the matrix 314.

The seed parcel 304A can be represented in a first indicia, such as a green color and/or green highlighting, to indicate to the user that the seed parcel 304A has been selected. The other parcels 304B-N are depicted in other indicia, such as varying shades or gradient of another color, like red. The other indicia can indicate a degree of correlation or connectivity between each of the parcels 304B-N and the seed parcel 304A. Moreover, as shown in FIG. 3A, sometimes a parcel may not be a continuous region overlaying the brain atlas data 302 and thus one or more separate blobs or other graphical elements may be visualized in a collection of voxels in a same indicia that make up the parcel.

As an illustrative example, parcels depicted in a darker shade of red can have a higher degree of correlation to the seed parcel 304A than parcels depicted in a lighter shade of red. In the GUI 300 of FIG. 3A, parcel 304E can have the highest degree of correlation to the seed parcel 304A since the parcel 304E appears in a darkest shade of red. Parcel 304F can have a second highest degree of correlation to the seed parcel 304A and is represented in a shade of red that is slightly less dark than the parcel 304E. Likewise, parcel 304D may have a third highest degree of correlation, parcel 304B may have a fourth highest degree of correlation, parcel 304N may have a fifth highest degree of correlation, and parcel 304C can have a sixth highest degree of correlation, or the lowest degree of correlation to the seed parcel 304A.

Although correlations and other connectivity metrics are shown between the seed parcel 304A and the other parcels 304B-N using color and shading of color, one or more other indicia may also be used. For example, each of the parcels 304B-N can be represented in a different color, where each color corresponds to a different degree of correlation. As another example, each of the parcels 304B-N and/or the seed parcel 304A can be represented in different patterns and/or hashes that can indicate degree of correlation.

Still referring to the GUI 300 in FIG. 3A, the GUI 300 can also include an anatomical controls menu 306. The anatomical controls menu 306 can be used by the user to adjust what structures are shown in the brain atlas data 302 for the particular patient, what views are shown, and/or how the brain atlas data 302 is shown in the GUI 300. For example, the user can adjust and select one or more different base scans, left and right sagittal, back and front coronal, bottom and top axial, low and high contrast, low and high saturation, and low and high parcel opacity. The user can also toggle between showing anatomical structures. Using the menu 306, the user can customize what information is presented in the GUI 300 and how the information is presented in order to facilitate the user's particular needs, interests, and/or decision-making process.

The GUI 300 can also include an export controls menu 308. Using the menu 308, the user can select what tracts, parcels, and/or ROI selections to export. Such information can be exported to another end user system. Such information can also be exported into another data format, which the user or other relevant users can view. The exported information can be used by the relevant user to make decisions in diagnoses, treatments, and/or therapies, as described throughout this disclosure.

The GUI 300 can also include a legend 309. The legend 309 can include a selectable option 310 to view correlations, or other connectivity metrics, amongst the parcels 304A-N within the matrix 314 (e.g., a connectivity matrix, or a matrix showing one or more other connectivity metrics described herein). Selecting the option 310 can cause the matrix 314 to be presented in a portion of the GUI 300. For example, the matrix 314 can be presented as overlaying a portion of the brain atlas data 302, as shown in the FIG. 3A.

The matrix 314 identifies, for each pair of parcels of multiple parcels 304A-N in the brain of a patient, the correlation (or other connectivity metric) between a measure of brain activity of the first parcel (e.g., the seed parcel 304A) of the pair of parcels and the measure of brain activity of the second parcel (e.g., any of the parcels 304B-N) of the pair of parcels. That is, each row and column of the matrix 314 can correspond to a parcel, and each element can have a value identifying the correlation between the parcel corresponding to the row of the element and the parcel corresponding to the column of the element. In some implementations, the matrix 314 can include ranges of one or more different colors. As an illustrative example, a first color can correspond to negative correlations and a second color can correspond to positive correlations. An intensity of the colors (e.g., shading) can also correspond to a magnitude of negative or positive correlations (e.g., low and high correlations).

In some implementations, the matrix 314 can show anomalous correlations amongst one or more pairs of parcels. In particular, the matrix 314 can visually identify elements that correspond to pairs of parcels whose correlations have been determined to be too variable (e.g., in a first indicia, such as a color or shade/gradient of color), elements that correspond to pairs of parcels whose correlations have been determined to be "normal" (e.g., in a second indicia, such as a color or shade/gradient of color), and elements that correspond to pairs of parcels whose correlations have been determined to be anomalous (e.g., in a third indicia, such as a color or shade/gradient of color).

The user can select what type of matrix they would like to view in the GUI 300. The matrix 314 can, for example, can show connectivity metrics other than correlation (e.g., electrical activity) between the parcels 304A-N. For example, the matrix 314 can show anomalous correlations (e.g., anomalous correlations of electrical activity) between the parcels 304A-N, as mentioned above. As another example, the matrix 314 can show a number of tracts connecting the parcels 304A-N. One or more other connectivity metrics may also be shown in the matrix 314. These one or more other connectivity metrics may also be visualized in 3D space using indicia such as different colors and categorizations, as described herein. The one or more connectivity metrics can include, but are not limited to, a number of tracts connecting two parcels, a degree to which a number of tracts connecting two parcels is considered "normal," a change in the number of tracts connecting two parcels when comparing two points in time, an fMRI time series comparison metric (e.g., correlations, concordance, cross correlation, anomalies, etc.), a change in fMRI signal when comparing two points in time (e.g., a change in number of tracts after a rehab course, an improvement in functional data after the rehab course, etc.), and one or more other network and/or relationship metrics.

The legend 309 can also include a filter 312. As shown in FIG. 3A, the filter 312 can be a slider. The user can adjust buttons or other features of the filter 312 to adjust what data is presented overlaying the brain atlas data 302 and/or how the data is presented in the GUI 300. For example, the filter 312 can be a bidirectional slider that includes two selectable and adjustable arrows. The user can click on and drag either of the arrows towards right and/or left sides of the filter 312 in order to adjust a range of correlation to depict as overlaying the brain atlas data 302 relative to the seed parcel 304A. The user can also toggle the filter 312 between defining an outside range of correlation and an inside range of correlation to depict overlaying the brain atlas data 302. When the user selects the outside range of correlation and drags the arrows to opposite ends of the filter 312 (or otherwise away from each other), any values in between the arrows may be excluded and therefore parcels having those values of correlation with the seed parcel 304A may be excluded from overlaying the brain atlas data 302. On the other hand, if the user selects the inside range of correlation and drags the arrows to opposite ends of the filter 312 (or otherwise away from each other), any values in between the arrows may be included and therefore parcels having only those values of correlation with the seed parcel 304A may be shown overlaying the brain atlas data 302.

The legend 309 also shows a first indicia in the filter 312 representing a high anti-correlation and a second indicia in the filter 312 representing high correlation. The first indicia can be a color, such as blue. The first indicia can also be presenting in varying shades to show a range of anti-correlation. The second indicia can also be a color, such as red and can be presented in varying shades to show a range of correlation. The legend 309 further indicates that the filter 312 can include a range of −1 to 0.2 in high anti-correlation and a range of 0.2 to 1 in high correlation. Overall, correlation can range from values of −1 to 1. Correlation values closer to −1 can be represented in a darker shade of blue in the filter 312 (and can represent higher degrees of anti-correlation) while correlation values closer to 0.2 can be represented in a lighter shade of blue or closer to a white color. Correlation values closer to 1 can be represented in a darker shade of red in the filter 312 (and can represent higher degrees of correlation) than correlation values closer to 0.2, which can be represented in a lighter shade of red or a color closer to the white color. A correlation value of 0, in some implementations, can be represented in white and can indicate that the parcels are uncorrelated.

One or more other ranges can also be used and presented in the legend 309 in reference to the filter 312. As an illustrative example, the user can adjust the slider 312 to define a threshold of $x<=-0.8$, which means a correlation threshold would be lower than −0.8 and higher than −1.0. As another example, the user can adjust the slider 312 to define a threshold of $x>=0.8$, which means a correlation threshold would be lower than 1.0 and higher than 0.8. As yet another example, the user can adjust the slider 312 to define a threshold of $-0.2<=x<=0.2$, which means a correlation threshold would be lower than 0.2 and higher than −0.2. As another example, the user can adjust the slider 312 to define a threshold of $x<=-0.8$, $x>=0.8$, which means a correlation threshold would be lower than −0.8 or higher than 0.8. The user can adjust the slider 312 in one or more other ways to define one or more other correlation thresholds for displaying parcels overlaying the brain atlas data 302 and/or in the matrix 314.

Furthermore, the shades of color represented in the filter 312 can also be depicted in the matrix 314 and/or the parcels 304B-N overlaying the brain atlas data 302 to visually show the degrees of correlation between the seed parcel 304A and the other parcels 304B-N.

For example, as shown in FIG. 3A, the seed parcel 304A is represented in the matrix 314 as highlighted column 316. The seed parcel 304A is identified as L_45. Each cell in the highlighted column 316 represents a degree of correlation that the seed parcel 304A has with the other parcels 304B-N overlaying the brain atlas data 302, where each of the other parcels 304B-N are represented by respective rows in the matrix 314. As shown in the column 316, the parcel L_45 (the seed parcel 304A) has high degrees of correlation with parcels L_6a, L_6v, L_3a, R_3a, R_6ma, R_6a, and R_24dv, as represented by the darker shade of red in the corresponding cells in the column 316 of the matrix 314. This darker shade of red corresponds to a value of high correlation as represented by the filter 312.

Figure 3B:
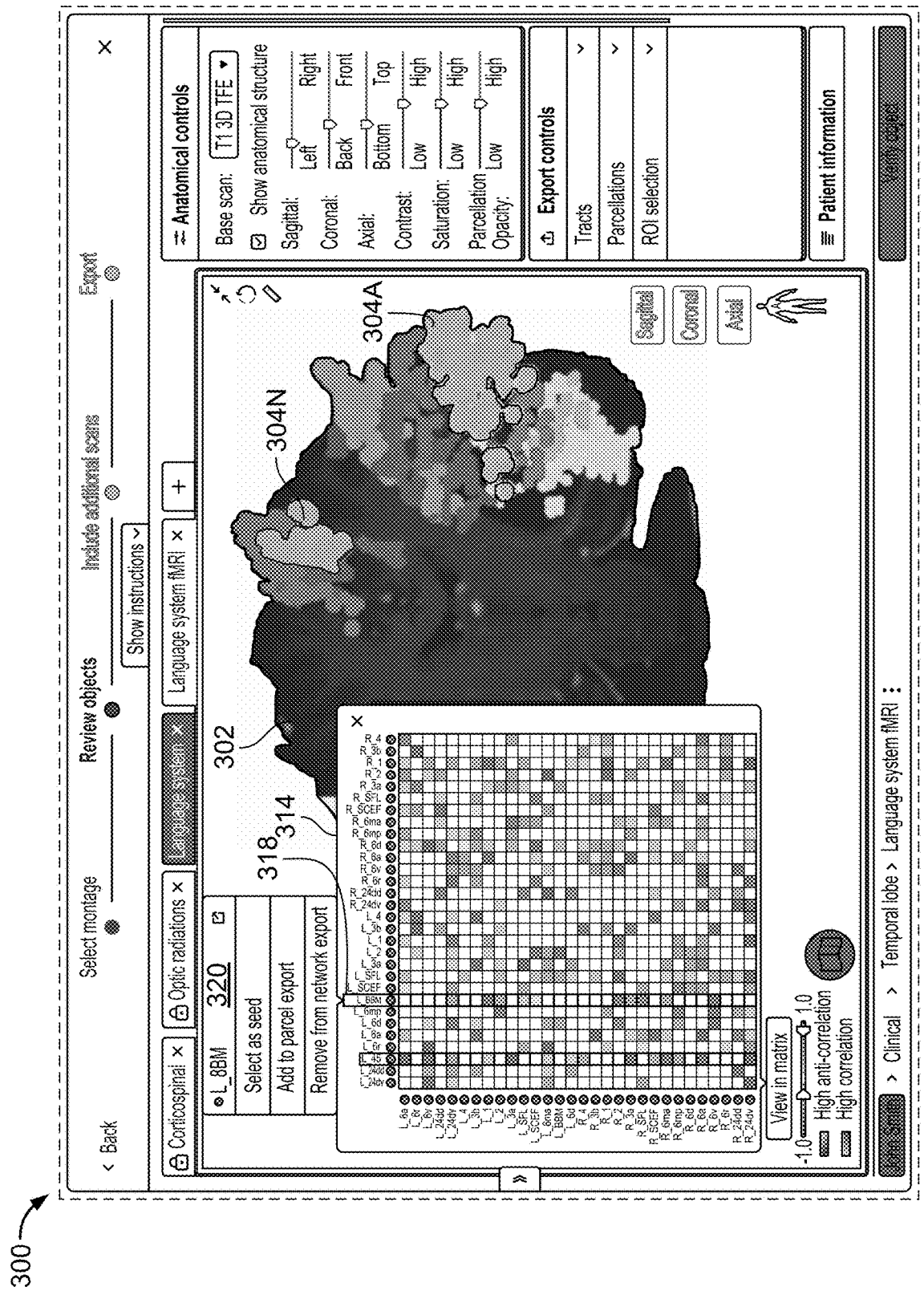
FIG. 3B illustrates the GUI display of FIG. 3A for user-selection of a new seed parcel using the connectivity matrix.

FIG. 3B illustrates the GUI display 300 of FIG. 3A for user-selection of a new seed parcel 304N using the connectivity matrix 314. As shown, the user can click on or select a column in the matrix 314 to identify a new seed parcel that corresponds to that column. When the user hovers over a column of interest 318, the column 318 can be highlighted in an indicia that is different than an indicia representing the column for the current seed parcel. The user can then click on the column of interest 318 to view a pop out window 320. The window 320 can be presented in the GUI 300 and can overlay a portion of at least one of the brain atlas data 302 and the matrix 304. The window 320 can indicate a name or other identifier for a parcel corresponding to the column of interest 318 as well as one or more selectable options. The selectable options can include, but are not limited to, selecting the parcel as a seed parcel, adding the parcel to an export, and/or removing the parcel from a network export. Adding the parcel to the export, as described further in reference to FIG. 3F, can include adding the parcel to a bottom-up parcel export. If the user selects the option to add to the parcel export, this option can be updated in the window 320 to now provide a selectable option to remove the parcel from the parcel export.

One or more other selectable options and/or information about the parcel can be presented in the window 320. For example, the window 320 can include an icon to link out to another tab and/or GUI that presents a description and other information about the parcel.

Additionally, as shown in FIG. 3B, the user has not yet selected the option to select the parcel corresponding to the column of interest 318 as the new seed parcel. Therefore, the current seed parcel 304A still remains in the indicia representing a seed parcel overlaying the brain atlas data 302, as described in reference to FIG. 3A. Similarly, the column in the matrix 314 corresponding to the seed parcel 304A still remains highlighted in the indicia described in FIG. 3A. However, now the parcel 304N, which corresponds to the column of interest 318, appears in another indicia overlaying the brain atlas data 302. The another indicia can be a highlighting around a perimeter of the parcel 304N. For example, the parcel 304N can be surrounded in a green line, halo, or other emphasis to differentiate the parcel 304N from the other parcels overlaying the brain atlas data 302. This can help the user visualize what parcel they are considering as the new seed parcel based on selection of the column of interest 318 in the matrix 314.

Figure 3C:
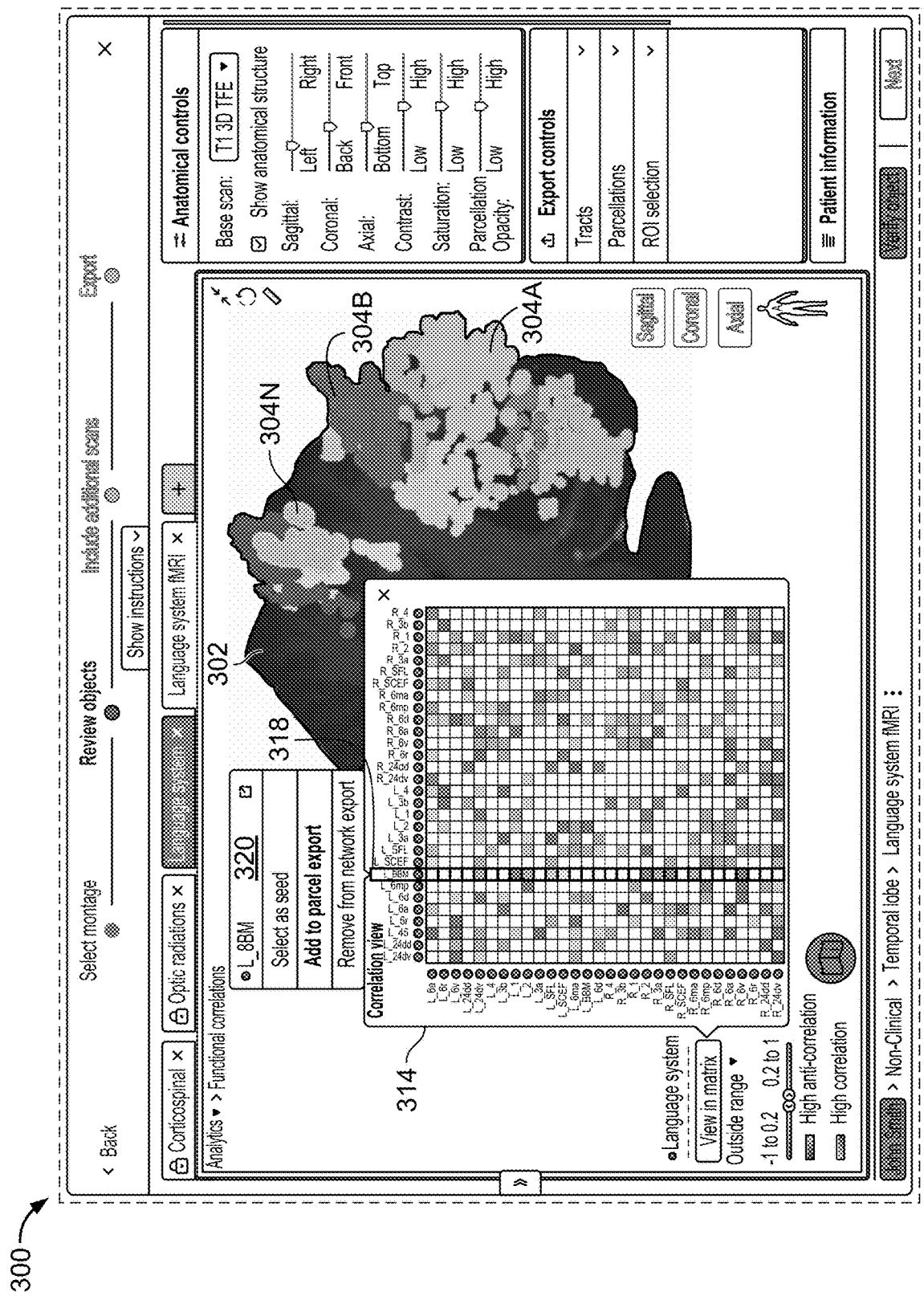
FIG. 3C illustrates the GUI display of FIG. 3A for viewing the user-selected seed parcel of FIG. 3B with the connectivity matrix and seed-connected parcels.

FIG. 3C illustrates the GUI display 300 of FIG. 3A for viewing the user-selected seed parcel 304N of FIG. 3B with the connectivity matrix 314 and seed-connected parcels. Once the user selects the option to select the parcel 304N corresponding to the column of interest 318 as the new seed parcel (refer to FIG. 3B), the GUI 300 is updated in FIG. 3C as shown and described herein. For example, the parcel 304A is no longer appearing in the indicia indicative of a seed parcel. Instead, the parcel 304A is now represented in an indicia (e.g., color) representing a degree of correlation between the new seed parcel 304N and the parcel 304A. Furthermore, the new seed parcel 304N is now represented in the indicia indicative of a seed parcel. The other parcels overlaying the brain atlas data 302 have also been updated in one or more other indicia to represent degrees of correlation between each of those parcels and the new seed parcel 304N. For example, parcel 304B, which was represented in a lighter shade of red when the seed parcel was the parcel 304A now appears in a darker shade of red when the new seed parcel 304N is selected. Thus, the parcel 304B has a higher degree of correlation with the seed parcel 304N and a lower degree of correlation with the parcel 304A when the parcel 304A was identified as the seed parcel (refer to FIG. 3A).

Additionally, as shown in FIG. 3B, now that the parcel 304N is selected as the seed parcel, one or more options in the pop out window 320 may no longer be selectable. For example, the user may only be able to add the selected seed parcel 304N to the parcel export. In some implementations, the option to select the seed in the pop out window 320 can be replaced with text indicating that the seed parcel has been selected. In some implementations, the user can hover over a greyed out option to "Select as seed," which can cause a tag to be displayed over a portion of the parcel 304N and/or a portion of the window 320. The tag can include some indication, such as "Already selected as seed parcel" to inform the user that the parcel 304N has been selected as the seed parcel. If, on the other hand, the parcel 304N has not been selected as the seed parcel, then the tag can include an indication such as "Select." The user can then click on this indication in order to identify the parcel 304N as the seed parcel.

As another example, the user can hover over a greyed out option to "Remove from network export," which can cause a tag to be displayed over a portion of the parcel 304N and/or a portion of the window 320. This tag can include some indication, such as "Cannot remove seed parcel from network export" to inform the user that the seed parcel 304N is to remain in the network export.

The column of interest 318 in the connectivity matrix 314 has also been updated to an indicia (e.g., highlighting, green highlighting, etc.) indicative that the column of interest 318 corresponds to the current, selected seed parcel 304N. The column corresponding to the parcel 304A is no longer represented in the indicia indicative of a seed parcel because the parcel 304A is no longer selected as the seed parcel in FIG. 3C. The indicia can also visually identify the selected column of interest 318 in any other way, including but not limited to outlining the selected column of interest 318, highlighting the selected column of interest 318, dimming unselected columns in the matrix, etc.

Although a column of the matrix 314 is selected in FIG. 3C, it is to be understood that the following description can also apply to rows of the matrix 314. Similarly, although a single column of the matrix 314 is selected, it is to be understood that the following description can also apply to any number of selected columns of the matrix 314.

As described herein, each column of the matrix 314 corresponds to a particular parcel of the brain of the patient, and can have a corresponding parcel identification IDN. The parcel identifications, depicted with the matrix 314 in FIG. 3C, may or may not be displayed for the user to view in the GUI 300. The user can select a desired column in any appropriate way, e.g., by clicking on the corresponding parcel identification number, or by clicking on any element of the column.

The GUI 300 can determine a parcel identification of the column selected by the user and send the parcel identification to a target generation system, e.g., the target generation system 270 depicted in FIG. 2B. The target generation system can also obtain brain atlas data 302 defining the parcels of the patient's brain. The target generation system can then determine, according to the parcel identification, a subset of the brain atlas data 302 that characterizes the parcel corresponding to the selected column of the matrix 314 (in the example of FIG. 3C, the parcel 304N). The target generation system can provide the subset of the brain atlas data 302 to the GUI 300 for presentation to the user.

Accordingly, the GUI 300 can use the subset of the brain atlas data 302 to generate the brain atlas data 302 shown and described in FIG. 3C.

Figure 3D:
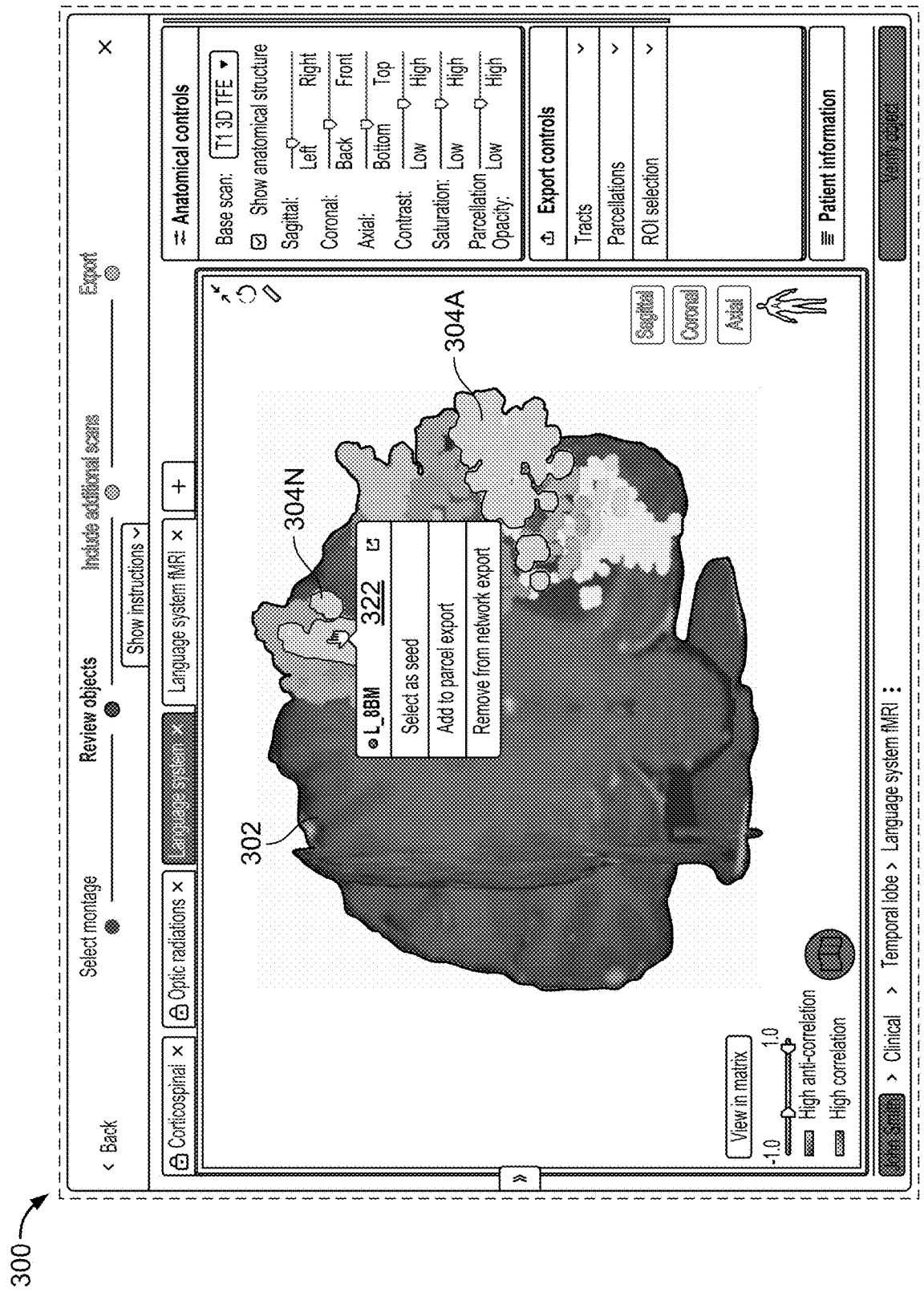
FIG. 3D illustrates the GUI display of FIG. 3A for user-selection of a seed parcel in 3D space.

FIG. 3D illustrates the GUI display 300 of FIG. 3A for user-selection of a seed parcel 304N in 3D space. FIGS. 3B-C referred to selecting the parcel 304N as the new seed parcel using the connectivity matrix 314. FIG. 3D depicts the user's ability to select a parcel directly from the brain atlas data 302 in order to identify that selected parcel as the new seed parcel. Moreover, the user can select a general region of the brain atlas data 302 for which they are interested. By selecting the general region, the GUI 300 can be updated to show a parcel located in that region represented in an indicia that indicates user-selection of that parcel.

The user can select or click on a parcel displayed as overlaying the brain atlas data 302, such as the parcel 304N. When the user selects the parcel 304N, a pop out window 322 can be presented in the GUI 300. The window 322 can, for example, be presented over a portion of the brain atlas data 302. The window 322 can identify the selected parcel 304N (e.g., by presenting a name or parcel identifier for the selected parcel 304N), information about the parcel, and one or more selectable options. The selectable options, as described in reference to FIG. 3B, can include selecting the parcel 304N as the new seed parcel, adding the parcel 304N to the parcel export, and/or removing the parcel 304N from the network export. As described in reference to FIG. 3B, the parcel 304N can be presented with an outline or other indicia when the parcel 304N is selected. This visualization can help the user understand which parcel they are looking at and considering as the new seed parcel. Once the user selects the option to select the parcel 304N as the seed parcel, then the parcel 304N can be updated and represented in the indicia representative of the seed parcel. The parcel 304A, which is the current seed parcel, can then be updated and presented in another indicia described throughout this disclosure that does not indicate that the parcel is the seed parcel. Refer to FIG. 3C for additional discussion about updating the parcels overlaying the brain atlas data 302 when a new seed parcel is selected by the user.

Figure 3E:
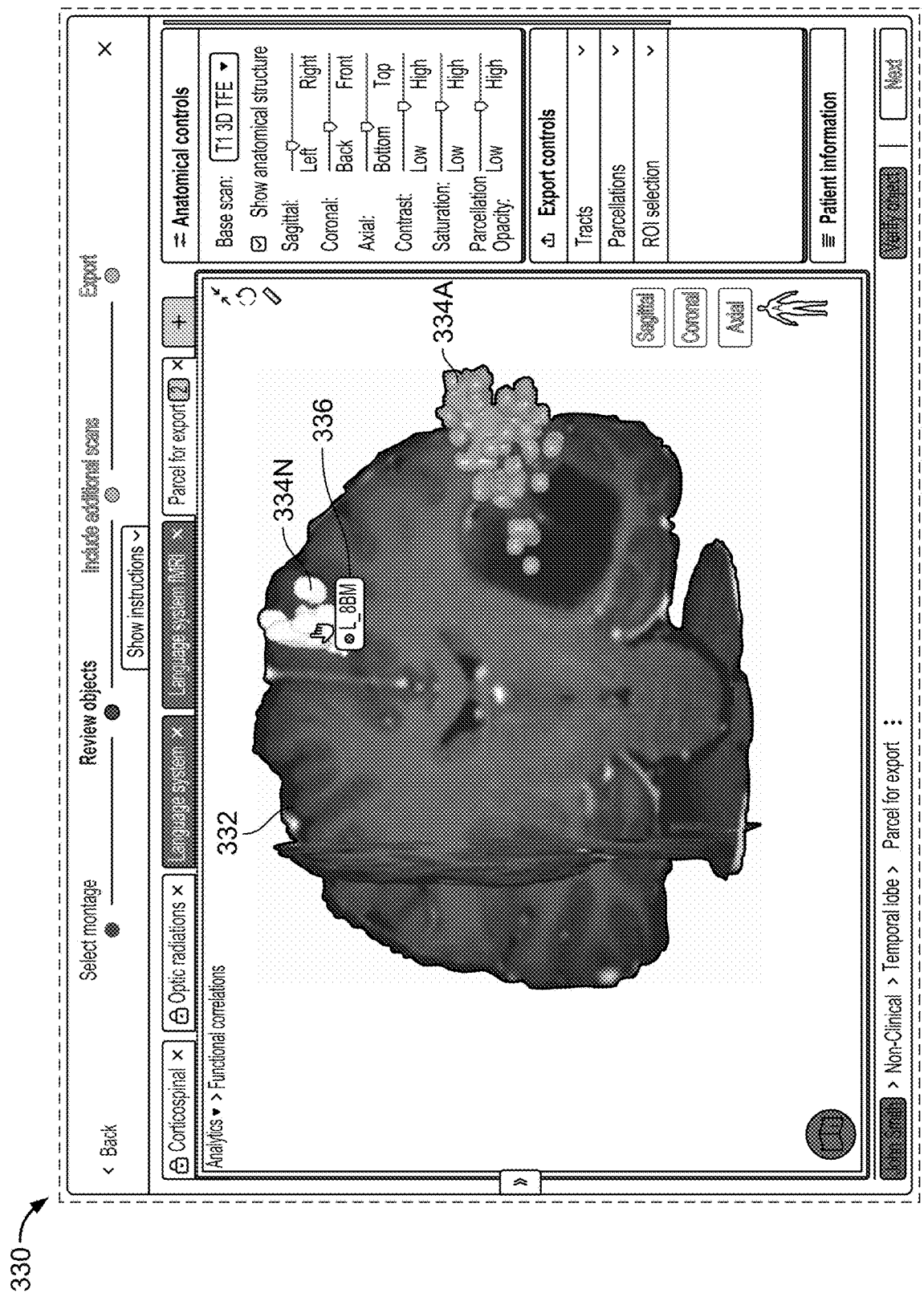
FIG. 3E illustrates a GUI display for viewing user-selected parcels for export in 3D space.

FIG. 3E illustrates a GUI display 330 for viewing user-selected parcels 334A and 334N for export in 3D space. As described in reference to FIGS. 3B and 3D, the user can select an option from a pop out window to add a selected parcel to the parcel export. The user can then view these selected parcels for export in the GUI 330. The user can navigate to the GUI 330 by selecting a tab or other option in a menu to view the GUI 330.

The user can select between a top-down network export in fMRI view and creating a bottom-up parcel export. Structural and fMRI views of the brain atlas data 302 are top-down network exports by default. Therefore, exporting either of these views can result in exporting all or most of what the user currently sees in those tabs (e.g., all of the parcels 304A-N shown overlaying the brain atlas data 302 in FIG. 3A). By interacting with the parcels 304A-N presented in the GUI 300, as described in reference to FIGS. 3A-D, the user can remove one or more of the parcels 304A-N from the network export. Thus, those one or more parcels may disappear from the matrix 314 (refer to FIG. 3A) and from the 3D view of the brain atlas data 302 in the GUI 300. Accordingly, the network export may not include those one or more parcels.

Additionally, by interacting with the parcels 304A-N presented in the GUI 300, as described in reference to FIGS. 3A-D, the user can also add a parcel to a bottom-up parcel export. Adding the parcel to the export can open a new tab, shown as the GUI 330 in FIG. 3F. Although tracts may be off by default, the user can also select to switch the tracts on. The user can add more parcels to the bottom-up parcel export, which can be reflected in the GUI 330.

The GUI 330 can present 3D brain atlas data 332, which can correspond to the brain atlas data 302 described in reference to FIGS. 3A-D. Here, only the exported parcels 334A and 334N overlay the 3D brain atlas data 332. This is because the user might have selected only parcels corresponding to the exported parcels 334A and 334N, such as parcels 304A and 304N, respectively, to be exported.

The exported parcels 334A and 334N can be represented in different indicia, such as different colors. The different indicia can be beneficial to assist the user in visualizing the three-dimensionality of each exported parcel 334A and 334N.

The user can also hover over (e.g., with a mouse) one of the exported parcels 334A and 334N to view additional information about that parcel 334A or 334N. The additional information can be presented in a tag 336. The tag 336 can be displayed over a portion of the parcel 334A or 334N that the user hovers over. The additional information can include a name or other identifier for the parcel 334A or 334N that the user hovers over.

Figure 3F:
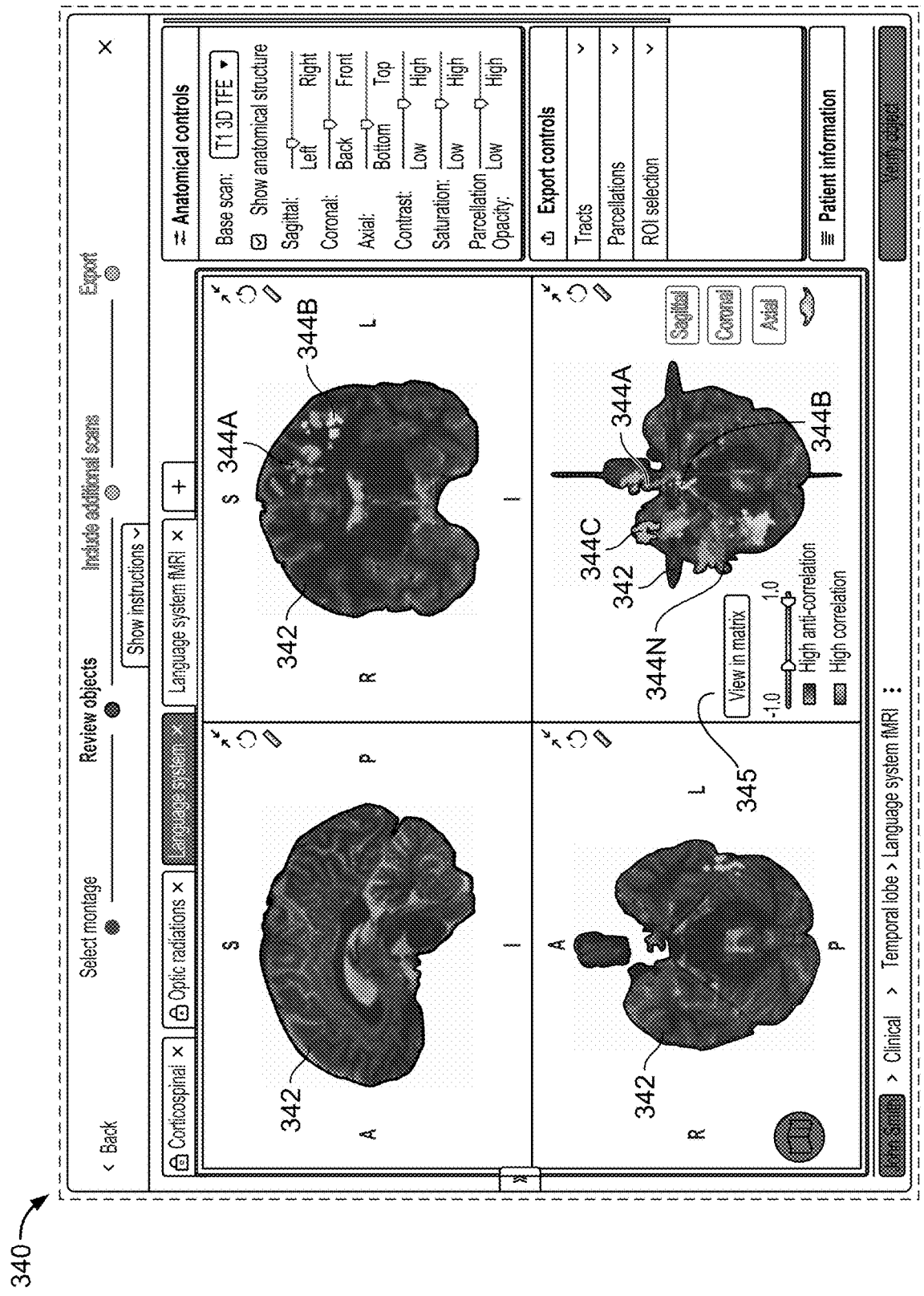
FIG. 3F illustrates a GUI display for viewing a seed parcel and seed-connected parcels in 2D space.

FIG. 3F illustrates a GUI display 340 for viewing a seed parcel 344C and seed-connected parcels 344A-N in 2D space. Brain atlas data 342 associated with a patient can be presented in 3D space, as described in reference to FIGS. 3A-E, as well as 2D space, as shown and described in reference to FIG. 3F. The brain atlas data 342 corresponds to the brain atlas data 302 described herein. Presenting the brain atlas data 342 in 2D space can be beneficial to present the user with a cross-section of a parcel as it relates to that specific slice of the patient's brain. Therefore, the user can view the underlying anatomy, which may help the user decide how to treat the patient. In the case of surgery, for example, the 2D view can help the user decide how to approach a tumor by going around parcels of interest.

In 2D space, the brain atlas data 342 can be presented from one or more angles, views, vantage points, sides, etc. in the GUI 340. The user can also adjust settings to display the brain atlas data 342 in one or more user-desired vantage points. As shown, in 2D space, not all of the parcels 344A-N may be visible in each vantage point, however the 2D view can show the user what parcels are present at a particular cross section of the brain atlas data 342. The 3D view of the brain atlas data 302, on the other hand, can show all the parcels up front and in view, even if one or more of those parcels extend backwards or towards an opposite end of the brain atlas data 302 than what is shown.

The parcels 344A-N can be represented in one or more indicia representative of degrees of correlation between a seed parcel and seed-connected parcels, as described in reference to FIGS. 3A-E. In the example of FIG. 3F, the parcel 344C is identified as the seed parcel. The parcel 344C therefore appears in the indicia (e.g., green color) indicative of a seed parcel. The parcels 344A, 344B, and 344N are represented in indicia, or shades of an indicia (e.g., shades of red, as described above), indicative of a degree of correlation between each of the parcels 344A, 344B, and 344N and the seed parcel 344C.

The GUI 340 can also include a legend 345, which can include one or more selectable options described in reference to FIG. 3A. For example, the legend 345 can include an option to view correlations or other connectivity metrics between the parcels 344A-N in a matrix. When the user selects this option, for example, a connectivity matrix can be presented as overlaying a portion of the brain atlas data 342 depicted in the GUI 340. Refer to FIG. 3A for additional discussion about the matrix and how the matrix can be used to view correlations between the parcels 344A-N and select a new seed parcel from the matrix. The legend 345 can also include a filter, such as a slider, for the user to adjust inner and/or outer ranges of correlation to show in 2D space. Refer to FIG. 3A for additional discussion about the legend 345.

Figure 4:
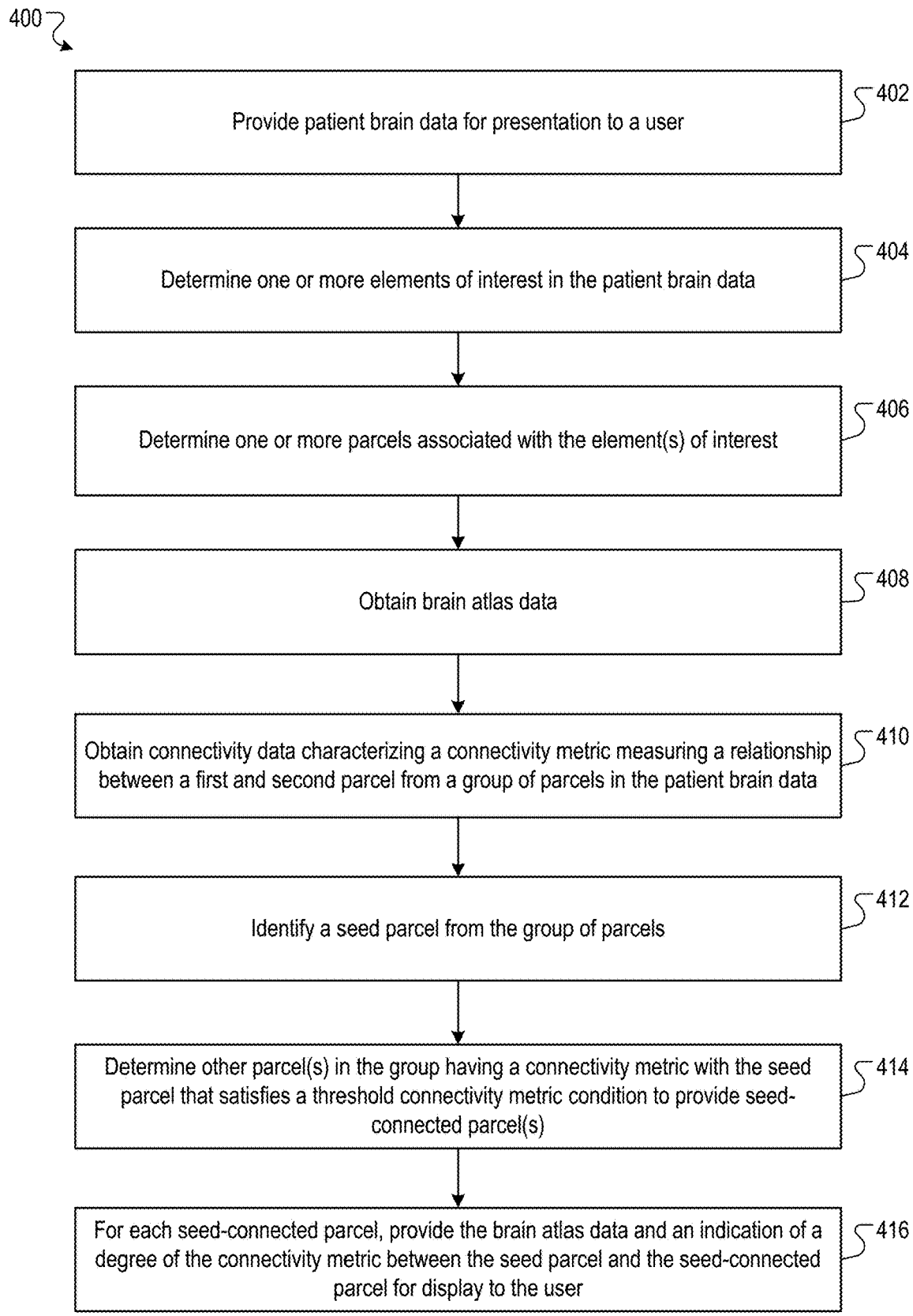
FIG. 4 is a flowchart of an example process for visualizing and interacting with connectivity metrics amongst parcels in patient brain data.

FIG. 4 is a flowchart of an example process 400 for visualizing and interacting with connectivity metrics amongst parcels in patient brain data. The process 400 can be implemented by one or more computer programs installed on one or more computers and programmed in accordance with this disclosure. For example, the process 400 can be performed by the computer system 100 depicted and described in FIG. 1A. The process 400 can be performed by one or more other computer systems, cloud-based systems, and/or network of devices and/or computers. For illustrative purposes, the process 400 is described from the perspective of a system of one or more computers.

Referring to the process 400, the system can provide patient brain data for presentation to a user in block 402. The patient brain data can include tractography data and/or connectivity data characterizing the brain of a patient. The patient brain data can be provided in a GUI display in which the user can select a network of parcels to process and view (e.g., language, motor, vision network, etc.). Refer to FIG. 1A for additional discussion about providing the patient brain data.

The connectivity data can characterize, for each pair of parcels including a first parcel and a second parcel from a set of multiple parcels, a degree of correlation between a measure of the brain activity of the first parcel and a measure of the brain activity of the second parcel in the brain of a patient. In some implementations, the connectivity data can specify a connectivity matrix and each position in the connectivity matrix characterizes a pair of parcels.

The system can determine one or more elements of interest in the patient brain data (block 404). The elements of interest can be determined based on user input received from the user's device. The elements of interest, for example, can include connectivity data between one or more parcels in the patient brain data. For example, the system can receive a selection from the user of one or more positions in a connectivity matrix characterizing correlation between pairs of parcels in the brain of the patient. As a particular example, the system can receive a selection of a column or a row of a connectivity matrix (refer to FIGS. 3B-C). As another example, the system can receive user input indicating selection of a parcel, area, or region of the patient brain data that is presented to the user in the GUI, as described in FIG. 3D. The user selection described in reference to block 404 can indicate the user's interest to select a particular parcel in the patient brain data as a seed parcel.

The system can then determine one or more parcels associated with the element(s) of interest in block 406. For example, the user can select a seed parcel or an indication representing a parcel that the user would like to set as the seed parcel. The system can then determine and identify a parcel associated with the element of interest as the seed parcel. As another example, the user can select a network of parcels (e.g., language, motor, vision network, etc.) to view in block 404. In block 406, the system can then identify one or more parcels in the patient brain data that are associated with the user-selected network.

The system can receive brain atlas data in block 408. The brain atlas data can be received before, during, or after one or more other blocks described in reference to the process 400 (e.g., the blocks 402-406). For example, the brain atlas data can be received with the patient brain data in block 402. The brain atlas data can be part of the patient brain data, in some implementations. As another example, the brain atlas data can be received/obtained after block 410, described below.

The brain atlas data can be a 2D and/or 3D view of a generic human brain and parcels in the user-selected network of parcels for the particular patient can be displayed as overlaying portions of the brain atlas data when presented to the user in a GUI.

In block 410, the system can obtain connectivity data characterizing a connectivity metric measuring a relationship between a first and second parcel from a group of parcels in the patient brain data. As described above in reference to block 402, the system can receive connectivity data as part of the patient brain data. The connectivity data can be associated with one or more connectivity metrics that measure relationships between parcels from the group of parcels in the user-selected network. In other words, the connectivity metric can measure the relationship between the first parcel and the second parcel in the patient's brain. The connectivity metric can also be considered a correlation metric, as described throughout this disclosure.

In some implementations, the connectivity metric can be based on a correlation of BOLD signals variation over time (e.g., electrical activity). In some implementations, the connectivity metric can be a degree to which the correlation of BOLD signals is anomalous (e.g., anomalous correlations of electrical activity). In yet some implementations, the connectivity metric can be based on a number of tracts connecting the first parcel and the second parcel. One or more other correlations can be used to define the connectivity metric, as described above.

The system can identify the first parcel as a seed parcel. The second parcel can be a seed-connected parcel, which means the second parcel can have some degree of connectivity with the first parcel, according to the connectivity data. In some implementations, the system can simply identify connectivity data between pairs of parcels in the group of parcels in block 410 without identifying any particular parcel as the seed parcel.

The system can identify a seed parcel from the group of parcels in block 412. A default parcel can be selected as the seed parcel for each type of network of parcels. For example, if the user selects a motion network of parcels, the system can identify which parcel in this network is the default seed parcel. If the default seed parcel is not present in the patient brain data, then the system can select the next-in-line default seed parcel. In some implementations, the user can provide input at the user's device indicating selection of a parcel in the network as the seed parcel. For example, the user can select a parcel from a list of parcels that can be chosen as the seed parcel for the particular network.

As another example, and as described in reference to FIGS. 3A-F, the user can select a parcel as the seed parcel from a connectivity matrix. Each position in the matrix can characterize a pair of parcels. To select the parcel from the connectivity matrix, the user can select a column or row of interest in the connectivity matrix. Each column and row can represent a different parcel in the user-selected network of parcels, as described herein. The user can also select the parcel directly from the brain atlas data presented in a GUI by selecting a parcel from the group of parcels visualized by overlaying the brain atlas data. As mentioned above in reference to block 410, the first parcel can also be the seed parcel.

In block 414, the system can determine one or more other parcels in the group having a connectivity metric with the seed parcel that satisfies a threshold connectivity metric condition to provide at least one seed-connected parcel. For example, the system can analyze the connectivity data obtained in block 410 and determine which other parcels have the connectivity metric with the seed parcel that was identified in block 412. The seed parcel can be considered the first parcel and any of the other parcels can be considered the second parcel, or seed-connected parcels.

In some implementations, the system can receive user input indicating selection of the threshold connectivity metric condition (e.g., using the filter 312 described in reference to FIG. 3A). In other words, the system can receive a filter criteria for the connectivity metric. The user can make the filter criteria using a filter, such as a slider, that is presented in the GUI (refer to the filter 312 in FIG. 3A). The user can provide input indicating at least one adjustment to the filter. For example, the at least one adjustment can include moving a first portion of the filter closer to a left end of the filter and moving a second portion of the filter closer to a right end of the filter. A third portion of the filter between the first and second portions can represent the threshold connectivity metric condition (e.g., correlations). In some implementations, such as when the user defines outer ranges of the degree of the connectivity metric using the filter, if the threshold connectivity metric condition is satisfied for the seed parcel and the seed-connected parcel, the correlation between the two parcels may be excluded from presentation with the brain atlas data. In some implementations, on the other hand when the user defines inner ranges of the degree of the connectivity metric using the filter, if the threshold connectivity metric condition is satisfied, then the correlation between the two parcels may be included for presentation with the brain atlas data.

The system can then use the user selection to determine which parcels satisfy such threshold condition and should be presented as the seed-connected parcels. The threshold connectivity metric condition can include inner and/or outer ranges of connectivity (e.g., inner and/or outer ranges of degrees of connectivity between the seed parcel and the other parcels in the user-selected network) to display in the GUI.

For each seed-connected parcel, the system can provide the brain atlas data and an indication of a degree of the connectivity metric between the seed parcel and the seed-connected parcel for display to the user (block 416). The indication of the degree of the connectivity metric can be displayed to the user as an overlay on a visualization of the brain atlas data. For example, as described in reference to FIGS. 3A-F, the seed parcel can be represented in a first indicia, such as a color, highlighting, outline, and/or pattern. The seed-connected parcel can be represented in a second indicia. The second indicia can be different than the first indicia. The second indicia can be a different color, highlighting, outline, and/or pattern. In some implementations, the second indicia can be a shade or gradient of the different color, highlighting, outline, and/or pattern indicating the degree of the connectivity metric. For example, as shown and described in FIG. 3A, a seed-connected parcel having a high degree of the connectivity metric can be represented in a dark shade of red while a seed-connected parcel having a low degree of the connectivity metric can be represented in a light shade of red. One or more other indicia can also be used to represent and display the seed parcel and the seed-connected parcel(s) to the user.

In some implementations, the system can also provide connectivity matrix data for display to the user in blocks 402 and/or 416. The connectivity matrix data can be based on the connectivity data described herein. As described above, for example, the connectivity matrix data can be a matrix showing degrees of connectivity between and amongst parcels in the user-selected network. The matrix can show the degrees of the particular connectivity metric from block 410. Refer to FIG. 3A for additional discussion about the matrix. Providing indications of the degree of the connectivity metric between the seed parcel and the seed-connected parcel can include providing a visual indication of a selected column or a selected row in the connectivity matrix, where the selected column or the selected row corresponds to the seed parcel. The visual indication can be a highlighting, outline, and/or color.

In some implementations, the system may take one or more actions in response to receiving a user selection in response to providing the brain atlas data and the indication of the degree of the connectivity metric between the seed parcel and the seed-connected parcel(s). When the user selects (e.g., clicks on) a parcel overlaying the brain atlas data, the system can provide a pop out window to be presented over a portion of the brain atlas data in the GUI. The pop out window can include one or more selectable options, such as an option to select the parcel as the seed parcel, an option to export the selected parcel, and/or information including a name or other identifier associated with the selected parcel. For example, as described in reference to FIGS. 3A-F, the user selection can include selecting a new parcel as the seed parcel. The system can then perform blocks 412-416 for the new seed parcel. As another example, the user selection can include selecting the option to add one or more parcels to a parcel export. In response, the system can add the one or more parcels to the parcel export and/or present the parcel export in another GUI display to the user with the selected parcel(s). As another example, the user selection can include selecting an option to remove one or more parcels from the network. In response, the system can remove the one or more parcels that are displayed as overlaying the brain atlas data in the GUI. Moreover, as described above, the user selection can include modifying one or more filter criteria or threshold connectivity metric conditions to adjust what parcels and/or degrees of the connectivity metric are displayed between the seed parcel and the seed-connected parcel(s) in the GUI. In response, the system can update the GUI by displaying the seed-connected parcel(s) in one or more different indicia that corresponds to the adjusted degree(s) of the connectivity metric. The system can also perform one or more other actions in response to receiving the user selection, as described throughout this disclosure.

In some implementations, one or more blocks in the process 400 may not be performed. For example, blocks 402-406 optionally may not be performed. In some implementations, one or more blocks in the process 400 can be performed in parallel. Moreover, in some implementations, one or more of the blocks in the process 400 may be performed in a different order.

Embodiments of the subject matter and the functional operations described herein can be implemented in digital electronic circuitry, in tangibly-embodied computer software or firmware, in computer hardware, including the structures disclosed and their structural equivalents, or in combinations of one or more of them. Embodiments of the subject matter described herein can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

As used in this disclosure, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described herein can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described herein can be implemented on a computer having a display device, e.g., a CRT (cathode ray tube) or LCD (liquid crystal display) monitor, for displaying information to the user and a keyboard and pointing device, e.g, a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described herein can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described herein, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this disclosure contains many specific implementation details, these should not be construed as limitations on the scope of any invention or on the scope of what may be claimed, but rather as descriptions of features that may be specific to particular embodiments of particular inventions. Certain features that are described in this disclosure in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain some cases, multitasking and parallel processing may be advantageous.

What is claimed is:

1. A method comprising:
    obtaining connectivity data characterizing, for each pair of parcels comprising a first parcel and a second parcel from a plurality of parcels, a degree of correlation between a measure of brain activity of the first parcel and a measure of brain activity of the second parcel in a brain of a patient;
    identifying a seed parcel in brain atlas data associated with the brain of the patient, wherein the seed parcel is a plurality of voxels that are logically grouped, the location and shape of the seed parcel is defined by the plurality of voxels assigned to the seed parcel;
    determining one or more other parcels in the plurality of parcels having a correlation metric with the seed parcel, wherein the correlation metric satisfies a threshold correlation condition, wherein the threshold correlation condition is adjustable based on user input and is used to identify correlations between the seed parcel and the one or more other parcels for presentation to the user; and
    providing indications of correlations between the seed parcel and the one or more other parcels over the brain atlas data for presentation to the user, wherein the connectivity data specifies a connectivity matrix and each position in the connectivity matrix characterizes a pair of parcels, the method further comprising:
    presenting the connectivity matrix in a portion of a GUI with the brain atlas data, wherein at least some positions in the connectivity matrix are represented in an indicia that visually represents at least several degrees of correlation between the pair of parcels;
    presenting anomaly correlation data, wherein the anomaly correlation data visually identifies at least one pair of parcels whose correlation is anomalous;
    receiving user column input indicating selection of at least one of a column of the connectivity matrix, wherein receiving user column input comprises selecting a plurality of cells; and
    identifying the seed parcel based on the user column input.

2. The method of claim 1, wherein providing indications of correlations between the seed parcel and the one or more other parcels over the brain atlas data for presentation to the user comprises:
    providing data representing the GUI to a user device for displaying the GUI to the user, wherein the interface comprises (i) a visual indication of the at least one of the selected column and a selected row of the connectivity matrix and (ii) a visual representation of the brain atlas data, wherein the seed parcel is represented in a first indicia and the one or more other parcels are represented in a second indicia, the second indicia being different than the first indicia.

3. The method of claim 1, further comprising:
    receiving user row input selection of at least one row of the connectivity matrix;
    providing, based on receiving the user column input and on receiving the user row input indicating selection of a parcel in the brain atlas data, a pop out window to be presented over a portion of the brain atlas data in the GUI, the pop out window including (i) a selectable option to export the selected parcel and (ii) information including a name or identifier associated with the selected parcel;
    receiving second user input indicating selection of the option to export the selected parcel; and
    generating a version of the brain atlas data with the selected parcel.

4. The method of claim 3, wherein the pop out window further includes a selectable option to identify the selected parcel as the seed parcel, the method further comprising:
    receiving user input indicating selection of the option to identify the selected parcel as the seed parcel; and
    identifying the seed parcel as the selected parcel.

5. The method of claim 1, wherein the seed parcel is represented in a first indicia, the first indicia being different than an indicia in which the one or more other parcels are represented.

6. The method of claim 1, further comprising:
    providing a filtering slider to be presented in the GUI with the brain atlas data;
    receiving second user input indicating at least one adjustment to the filtering slider, wherein the at least one adjustment comprises moving a first portion of the filtering slider closer to a first end of the filtering slider and moving a second portion of the filtering slider closer to a second end of the filtering slider that is opposite the first end, wherein a third portion of the filtering slider between the first portion and the second portion represents correlations between the seed parcel and the one or more other parcels that are excluded from presentation over the brain atlas data; and
    providing indications of correlations between the seed parcel and a subset of the one or more other parcels where the correlations satisfy the at least one adjustment to the filtering slider, wherein the indications of correlations are provided for presentation over the brain atlas data.

7. The method of claim 1, wherein the indicia is a color.

8. The method of claim 7, wherein positions in the connectivity matrix that are represented in darker shades of color visually represent higher degrees of correlation between corresponding pairs of parcels and positions in the connectivity matrix that are represented in lighter shades of color visually represent lower degrees of correlation between corresponding pairs of parcels.

9. The method of claim 7, wherein positions in the connectivity matrix that are represented in a first color visually represent higher degrees of correlation between corresponding pairs of parcels and positions in the connectivity matrix that are represented in a second color visually represent lower degrees of correlation between corresponding pairs of parcels.

10. The method of claim 9, wherein the first color is different than the second color.

11. The method of claim 6, wherein the first portion of the filtering slider is presented in a first indicia, and the second portion of the filtering slider is presented in a second indicia.

12. The method of claim 11, wherein the first and second indicia are different colors.

13. The method of claim 11, wherein the first, and second indicia are different shades of a same color, wherein the different shades of the color represent a range of correlation or anti-correlation between the seed parcel and the one or more other parcels.

14. The method of claim 11, wherein:
the first indicia includes different shades of a first color, wherein darker shades of the first color represent higher degrees of anti-correlation and lighter shades of the first color represent lower degrees of anti-correlation, and
the second indicia includes different shades of a second color, wherein darker shades of the second color represent higher degrees of correlation and lighter shades of the second color represent lower degrees of correlation.

15. The method of claim 1, wherein the threshold correlation condition is equivalent to a normalized value of at least 0.2.

16. The method of claim 1, wherein the seed parcel is not a continuous region overlaying the brain atlas data and wherein the display of the seed parcel comprises a plurality of graphical elements that form a collection of voxels in a same indicia.

17. The method of claim 1, wherein the method further comprises:
obtaining normal correlation data that identifies, for each pair of parcels, a normal range of values for the correlation between the pair of parcels, the normal range determined according to the correlation between the pair of parcels measured in the respective brain of multiple other patients; and
based on the normal correlation data, determining one or more pairs of parcels in the connectivity data whose correlation is anomalous.

18. A method comprising:
obtaining connectivity data characterizing, for each pair of parcels comprising a first parcel and a second parcel from a plurality of parcels, a degree of correlation between a measure of brain activity of the first parcel and a measure of brain activity of the second parcel in a brain of a patient;
identifying a seed parcel in brain atlas data associated with the brain of the patient, wherein the seed parcel is a plurality of voxels that are logically grouped, the location and shape of the seed parcel is defined by the plurality of voxels assigned to the seed parcel;
determining one or more other parcels in the plurality of parcels having a correlation metric with the seed parcel, wherein the correlation metric satisfies a threshold correlation condition, wherein the threshold correlation condition is adjustable based on user input and is used to identify correlations between the seed parcel and the one or more other parcels for presentation to the user; and
providing indications of correlations between the seed parcel and the one or more other parcels over the brain atlas data for presentation to the user, wherein the connectivity data specifies a connectivity matrix and each position in the connectivity matrix characterizes a pair of parcels, the method further comprising:
presenting the connectivity matrix in a portion of a GUI with the brain atlas data, wherein at least some positions in the connectivity matrix are represented in an indicia that visually represents at least several degrees of correlation between the pair of parcels;
presenting anomaly correlation data, wherein the anomaly correlation data visually identifies at least one pair of parcels whose correlation is anomalous;
receiving user row input indicating selection of at least one row of the connectivity matrix, wherein receiving user row input comprises selecting a plurality of cells; and
identifying the seed parcel based on the user row input.

* * * * *